United States Patent
Lim et al.

(10) Patent No.: US 10,906,922 B2
(45) Date of Patent: Feb. 2, 2021

(54) HETEROCYCLIC COMPOUND AND ORGANIC SOLAR CELL COMPRISING SAME

(71) Applicant: LG CHEM, LTD., Seoul (KR)

(72) Inventors: Bogyu Lim, Daejeon (KR); Jaechol Lee, Daejeon (KR); Junghyun Park, Daejeon (KR); Donggu Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 100 days.

(21) Appl. No.: 15/557,972

(22) PCT Filed: Apr. 20, 2016

(86) PCT No.: PCT/KR2016/004109
§ 371 (c)(1),
(2) Date: Sep. 13, 2017

(87) PCT Pub. No.: WO2016/171465
PCT Pub. Date: Oct. 27, 2016

(65) Prior Publication Data
US 2018/0057515 A1    Mar. 1, 2018

(30) Foreign Application Priority Data
Apr. 20, 2015 (KR) .................. 10-2015-0055432

(51) Int. Cl.
| | | |
|---|---|---|
| *C07F 7/08* | (2006.01) |
| *C07F 7/02* | (2006.01) |
| *H01L 51/42* | (2006.01) |
| *C07D 519/00* | (2006.01) |
| *C09B 69/00* | (2006.01) |
| *H01L 51/00* | (2006.01) |

(52) U.S. Cl.
CPC .......... *C07F 7/0838* (2013.01); *C07D 519/00* (2013.01); *C07F 7/02* (2013.01); *C09B 69/008* (2013.01); *H01L 51/0068* (2013.01); *H01L 51/0069* (2013.01); *H01L 51/0072* (2013.01); *H01L 51/0094* (2013.01);
(Continued)

(58) Field of Classification Search
CPC ... H01L 51/0062; H01L 51/0065–0074; H01L 51/42–448; H01L 51/50–5234
See application file for complete search history.

(56) References Cited

U.S. PATENT DOCUMENTS

| | | |
|---|---|---|
| 5,331,183 A | 7/1994 | Sariciftci et al. |
| 5,454,880 A | 10/1995 | Sariciftci et al. |

(Continued)

FOREIGN PATENT DOCUMENTS

| | | | |
|---|---|---|---|
| CN | 103087083 A | * | 5/2013 |
| CN | 104119355 B | * | 5/2016 |

(Continued)

OTHER PUBLICATIONS

Z. Li, et al., "Solution processable rhodanine-based small molecule organic photovoltaic cells with a power conversion efficiency of 6.1%", Advanced Energy Materials 2, p. 74-77 (Year: 2012).*

(Continued)

*Primary Examiner* — Eric R Smith
(74) *Attorney, Agent, or Firm* — Myers Bigel, P.A.

(57) ABSTRACT

The present specification relates to a heterocyclic compound and an organic solar cell including the same.

10 Claims, 7 Drawing Sheets

(52) U.S. Cl.
CPC .......... *H01L 51/42* (2013.01); *H01L 51/0071* (2013.01); *H01L 51/4253* (2013.01)

(56) References Cited

U.S. PATENT DOCUMENTS

| | | | |
|---|---|---|---|
| 9,293,718 B2 | 3/2016 | Hayoz | |
| 2010/0294351 A1* | 11/2010 | Holmes | H01L 51/4253 |
| | | | 136/255 |
| 2011/0203649 A1* | 8/2011 | Konemann | C07D 241/38 |
| | | | 136/255 |
| 2014/0142308 A1* | 5/2014 | Chen | C07D 333/22 |
| | | | 544/296 |

FOREIGN PATENT DOCUMENTS

| | | |
|---|---|---|
| KR | 10-2015-0001792 A | 1/2015 |
| KR | 10-2015-0027344 A | 3/2015 |
| WO | 2007-003520 A1 | 1/2007 |

OTHER PUBLICATIONS

Machine translation of CN103087083A (Year: 2013).*
J. A. Love et al., "Silaindacenothiophene-based molecular donor: Morphological features and use in the fabrication of composition-ally tolerant, high-efficiency bulk heterojunction solar cells", Journal of the American Chemical Society 136, p. 3597-3606 (Year: 2014).*
R. S. Ashraf et al., "The influence of polymer purification on photovoltaic device performance of a series of indacenodithiophene donor polymers", Advanced Materials 25, p. 2029-2034 (Year: 2013).*
Machine translation of CN104119355B.*
D. Wang, et al., "Rational design and characterization of high-efficiency planar A-pi-D-pi-A type electron donors in small molecule organic solar cells: A quantum chemical approach", Materials Chemistry and Physics 145, p. 387-396 (Year: 2014).*
T. W. Holcombe, et al., "A structural study of DPP-based sensitizers for DSC applications", Chemical Communications 48, p. 10724-10726 (2012). (Year: 2012).*
Extended European Search Report corresponding to European Patent Application No. 16783398.7 dated Aug. 16, 2018. (6 pages).
Bai et al. "A bipolar small molecule based on indacenodithiophene and diketopyrrolopyrrole for solution processed organic solar cells" Journal of Materials Chemistry A 2:778-784 (2014).
Oh, J. H. et al., "Tuning polarity and improving charge transport in organic semiconductors", Proceedings of SPIE, 2013, 8831, 883112-1 to 883112-8.
Lee, J. et al., "Siloxane-based hybrid semiconducting polymers prepared by fluoride-mediated Suzuki polymerization", Angewandte Chemie, International Edition, Feb. 12, 2015, 54, 15, 4657-4660.

* cited by examiner

[Figure 1]
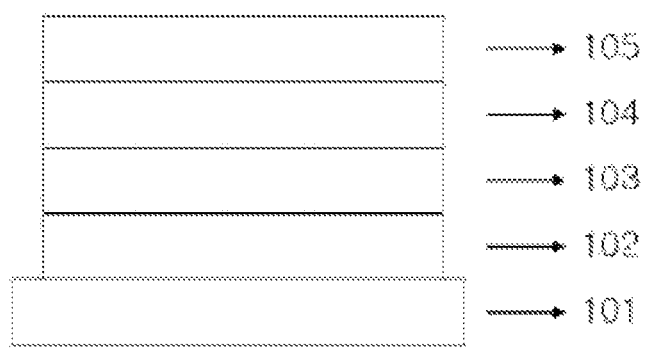
[Figure 2]
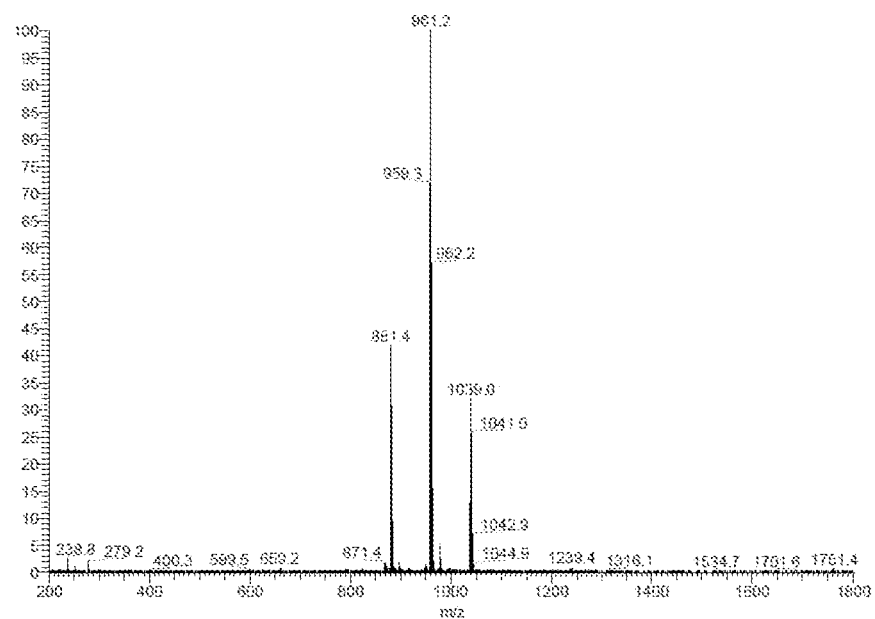

[Figure 3]
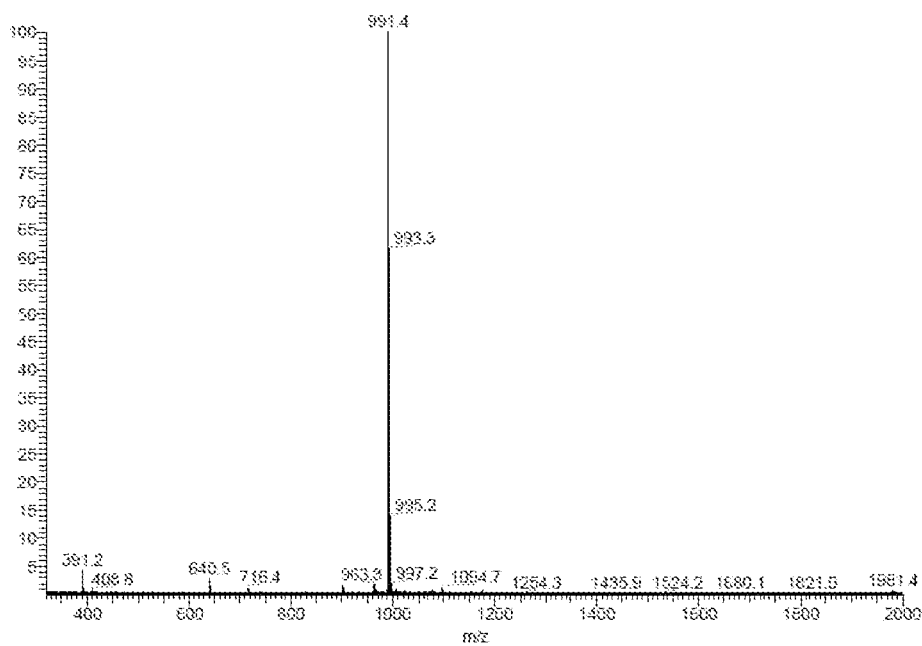
[Figure 4]
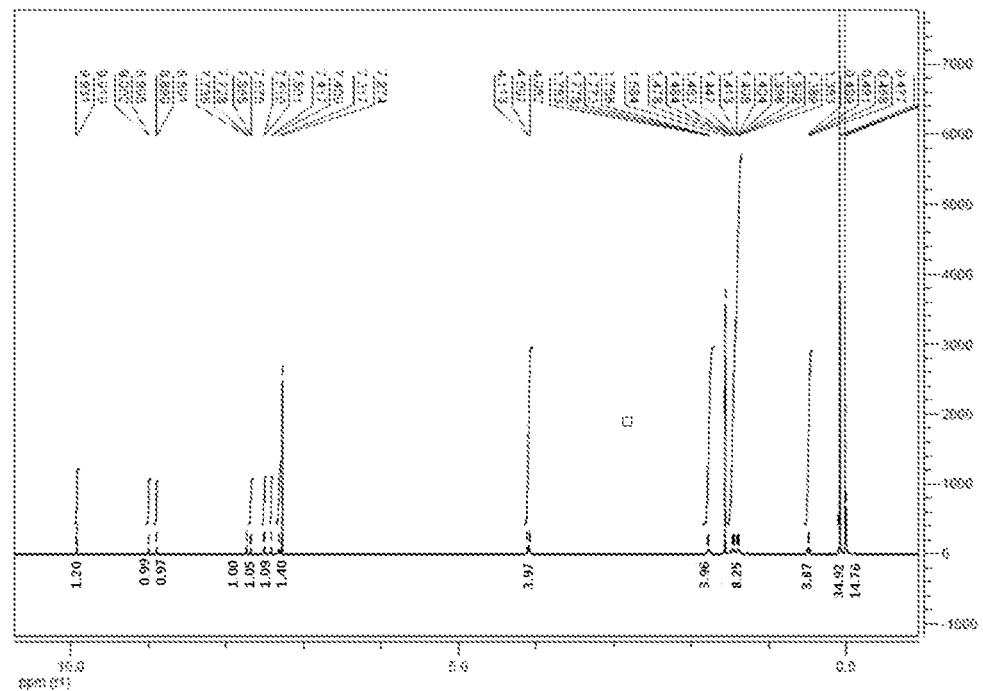

[Figure 5]
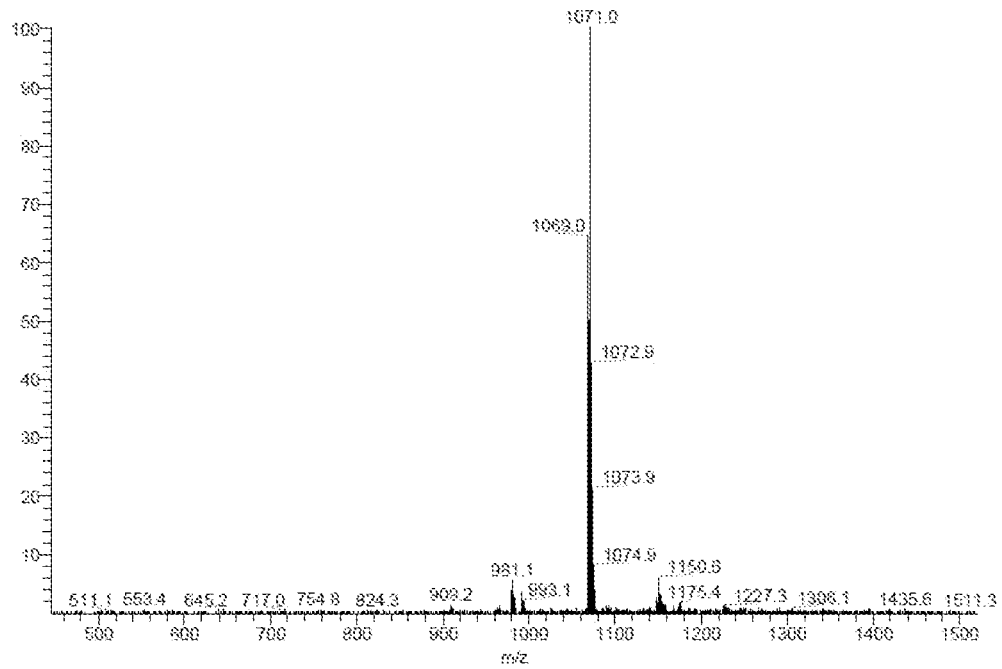
[Figure 6]
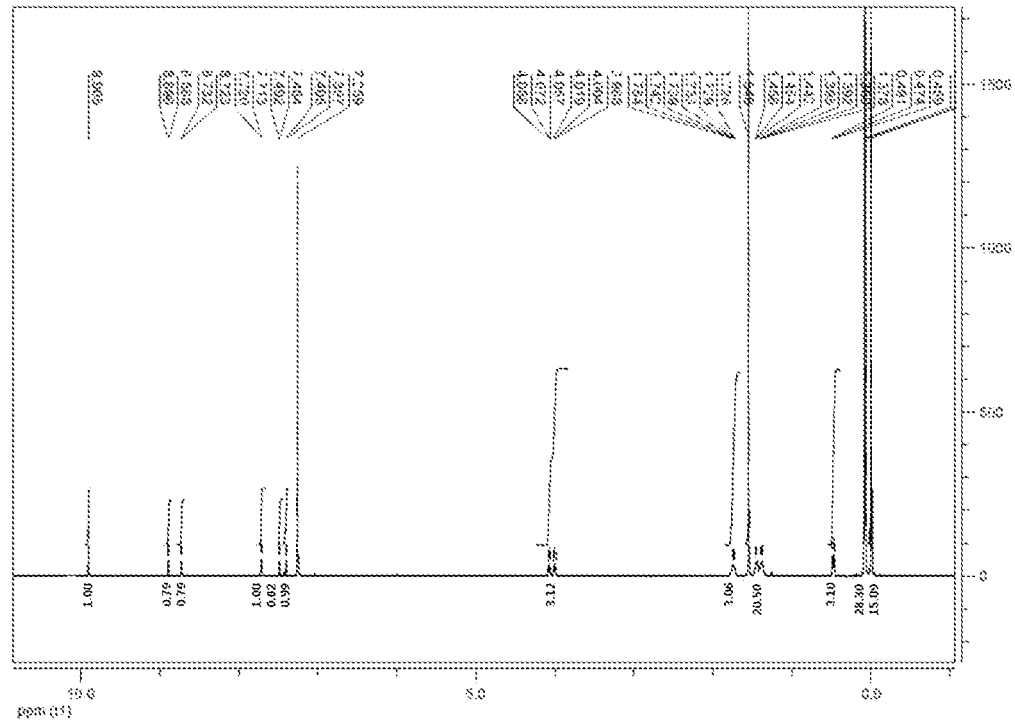

[Figure 7]
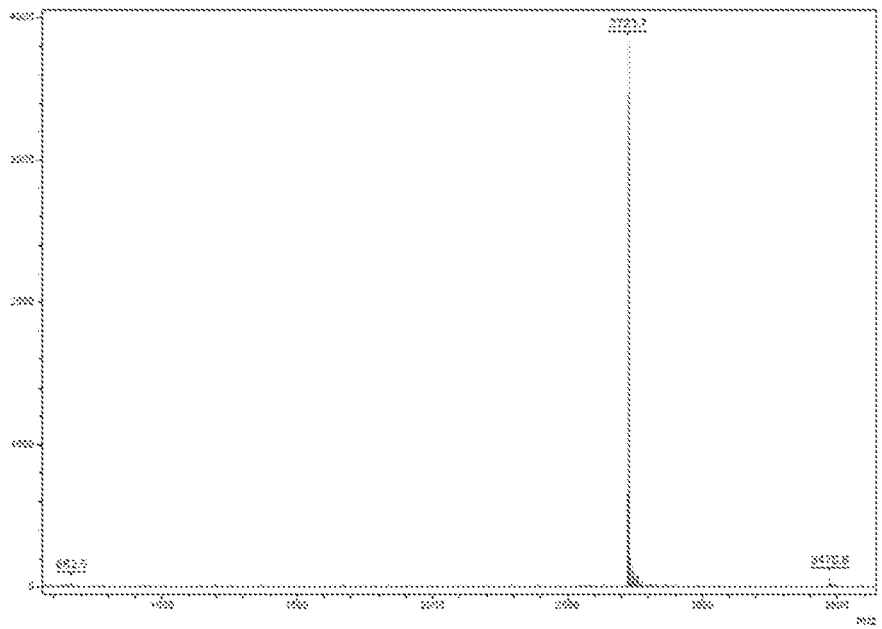
[Figure 8]
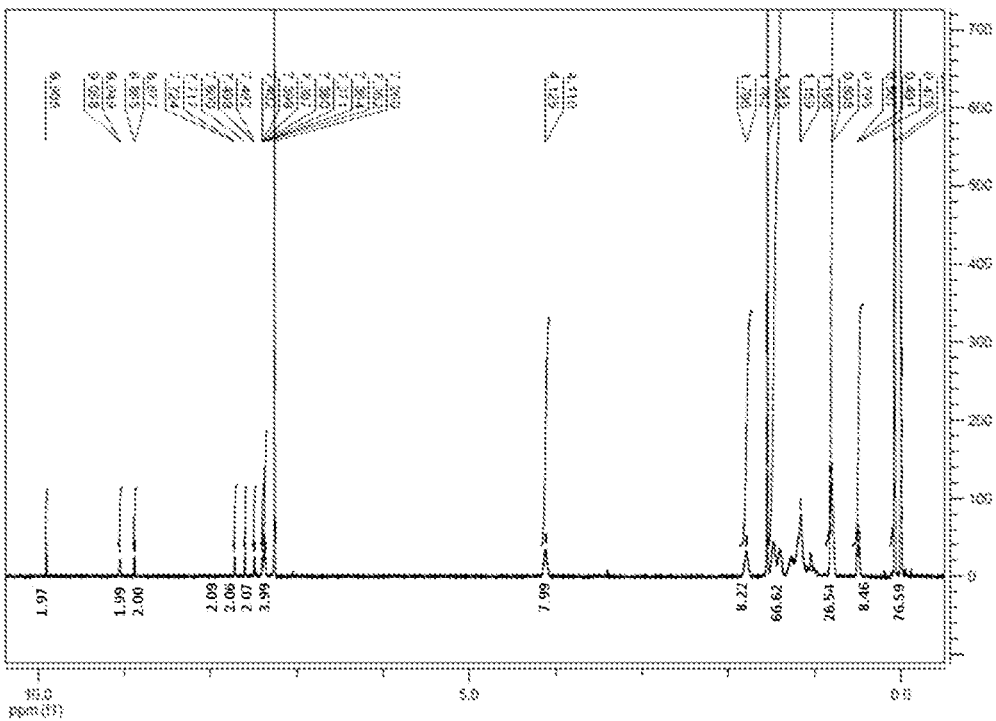

[Figure 9]
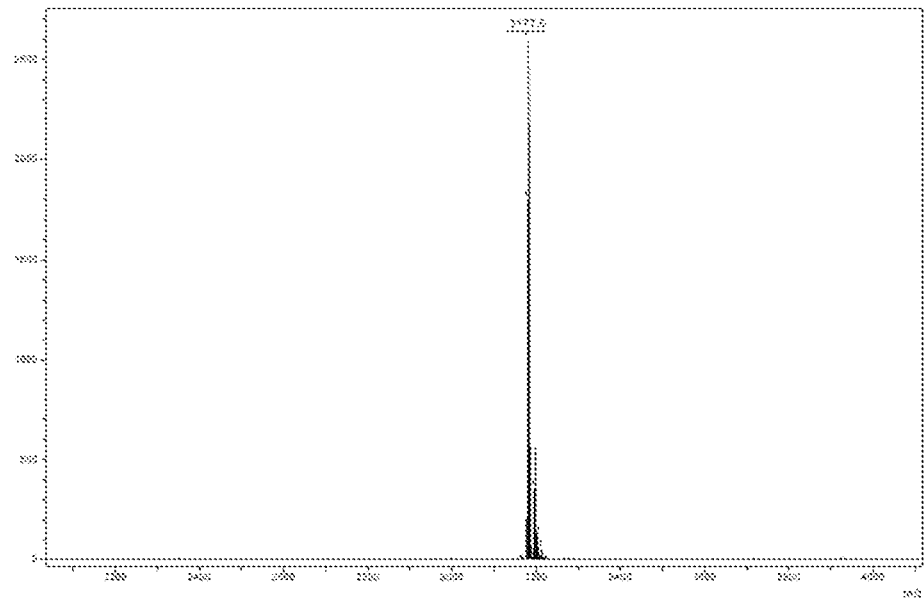
[Figure 10]
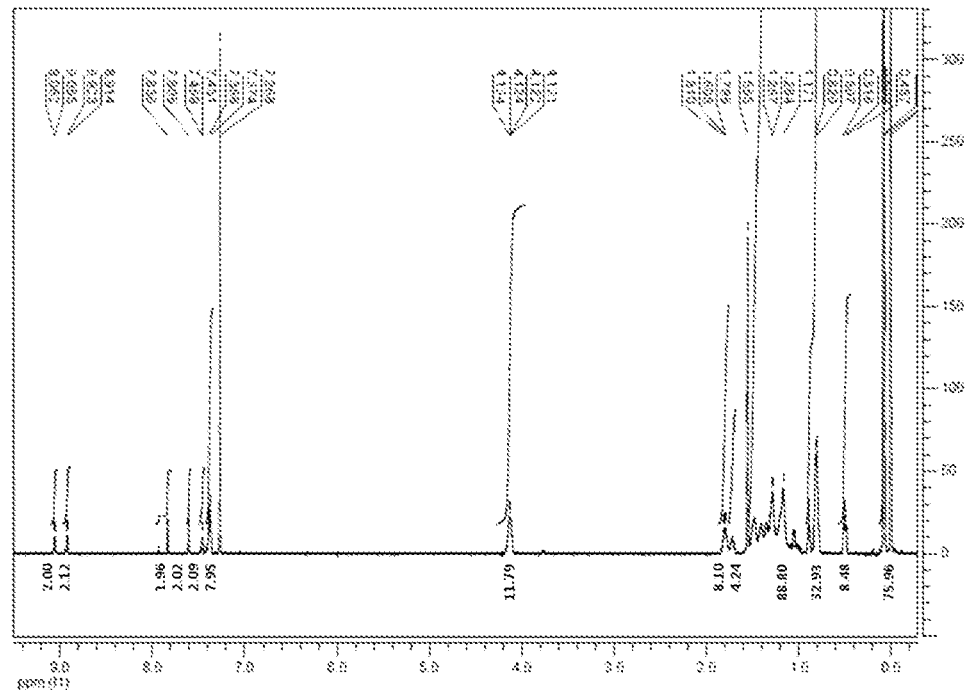

[Figure 11]
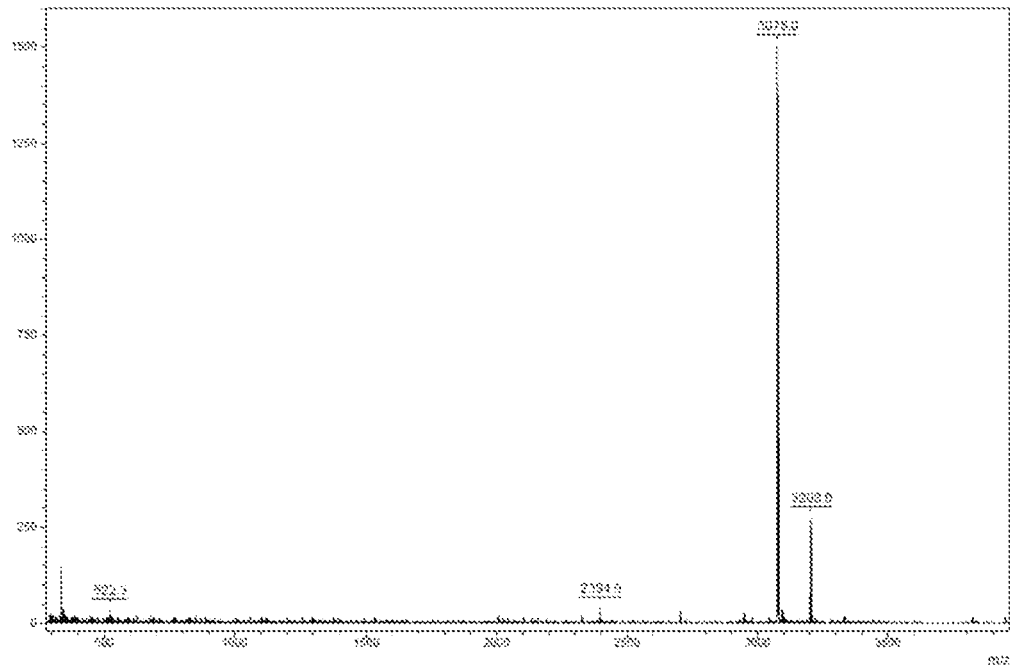
[Figure 12]
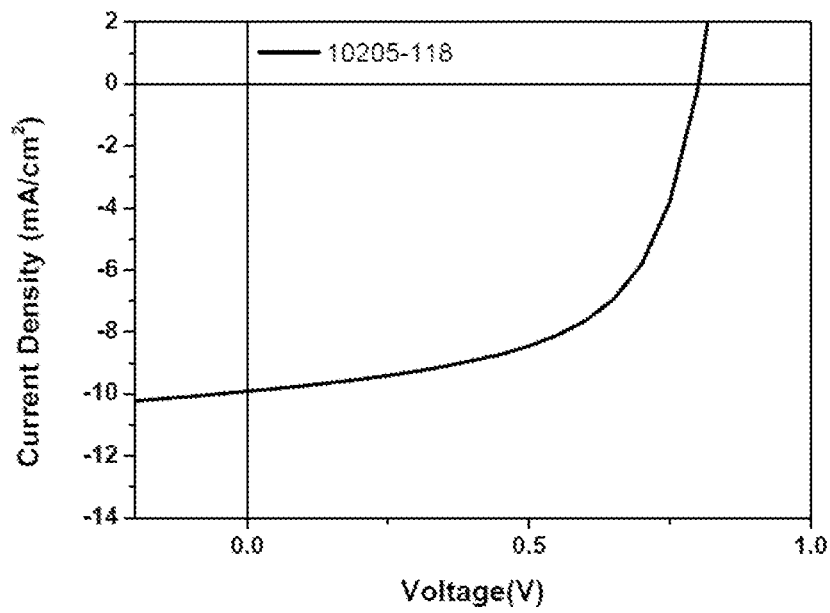

[Figure 13]
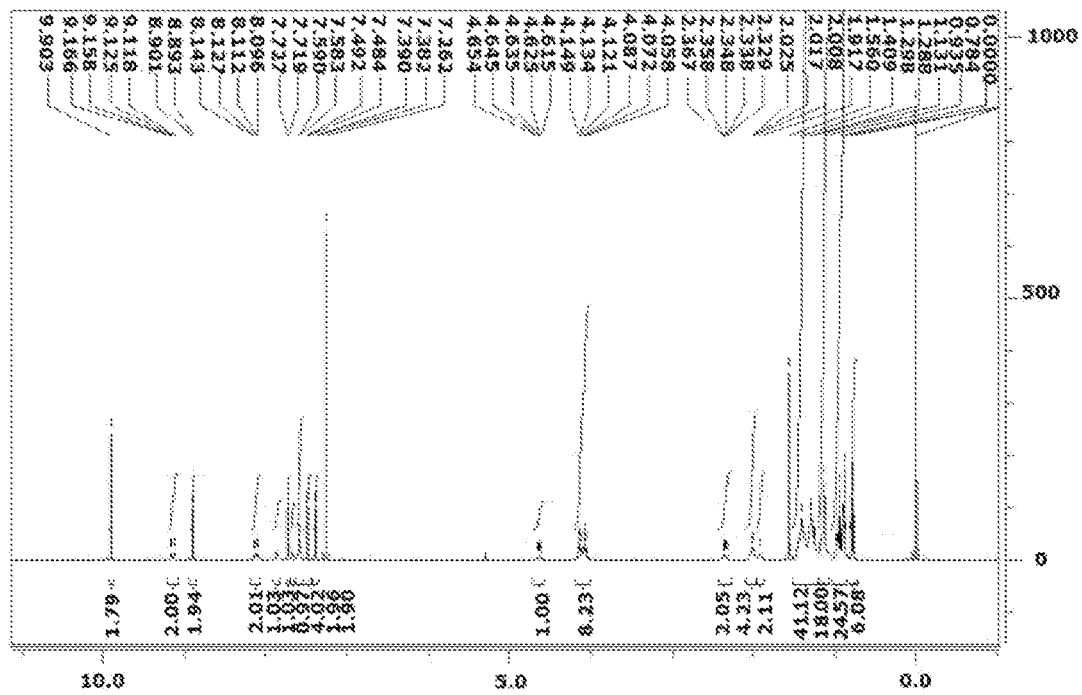
[Figure 14]
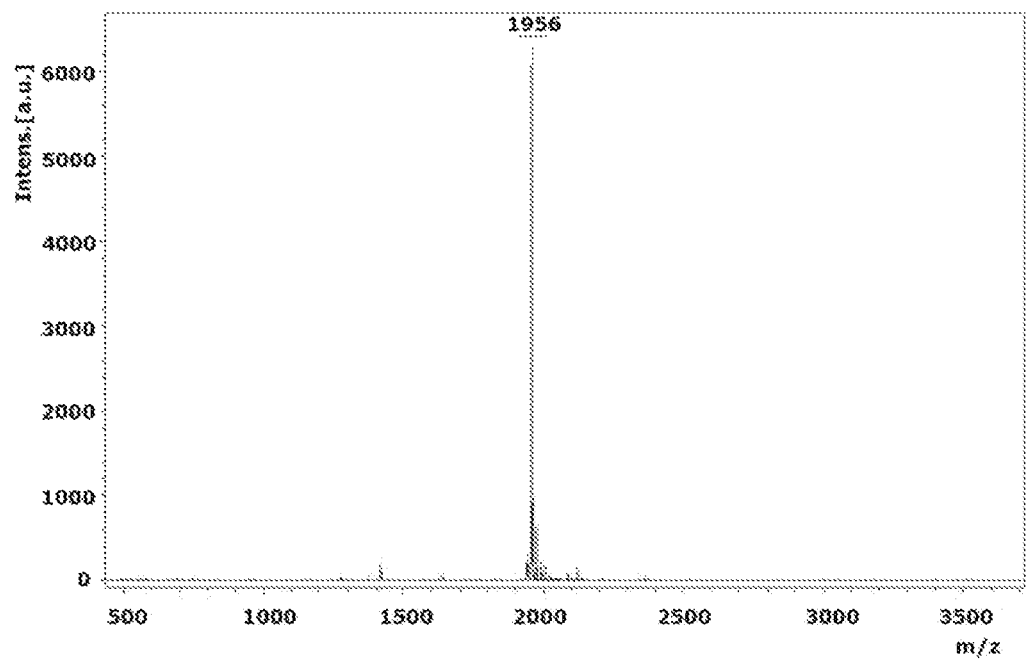

HETEROCYCLIC COMPOUND AND ORGANIC SOLAR CELL COMPRISING SAME

The present specification is a National Stage Entry of International Application No. PCT/KR2016/004109 filed on Apr. 20, 2016, which claims priority to and the benefit of Korean Patent Application No. 10-2015-0055432 filed in the Korean Intellectual Property Office on Apr. 20, 2015, the entire contents of which are incorporated herein by reference.

TECHNICAL FIELD

The present specification claims priority to and the benefit of Korean Patent Application No. 10-2015-0055432 filed in the Korean Intellectual Property Office on Apr. 20, 2015, the entire contents of which are incorporated herein by reference.

The present specification relates to a heterocyclic compound and an organic solar cell including the same.

BACKGROUND ART

A solar cell is a device which may directly convert solar energy into electric energy by applying a photovoltaic effect. A solar cell may be divided into an inorganic solar cell and an organic solar cell, depending on the materials constituting a thin film. Typical solar cells are made through a p-n junction by doping crystalline silicon (Si), which is an inorganic semiconductor. Electrons and holes generated by absorbing light diffuse to p-n junction points and move to an electrode while being accelerated by the electric field. The power conversion efficiency in this process is defined as the ratio of electric power given to an external circuit and solar power entering the solar cell, and currently, the efficiency have reached approximately 24% when measured under a standardized virtual solar irradiation condition. However, since inorganic solar cells in the related art have already shown the limitation in economic feasibility and material demands and supplies, an organic semiconductor solar cell, which is easily processed and inexpensive and has various functionalities, has come into the spotlight as a long-term alternative energy source.

For the solar cell, it is important to increase efficiency so as to output as much electric energy as possible from solar energy. In order to increase the efficiency of the solar cell, it is important to generate as many excitons as possible inside a semiconductor, but it is also important to pull the generated charges to the outside without loss. One of the reasons for the charge loss is the dissipation of generated electrons and holes due to recombination. Various methods have been proposed to deliver generated electrons and holes to an electrode without loss, but additional processes are required in most cases, and accordingly, manufacturing costs may be increased.

DETAILED DESCRIPTION OF THE INVENTION

Technical Problem

An object of the present specification is to provide a heterocyclic compound and an organic solar cell including the same.

Technical Solution

The present specification provides a heterocyclic compound represented by the following Chemical Formula 1.

[Chemical Formula 1]

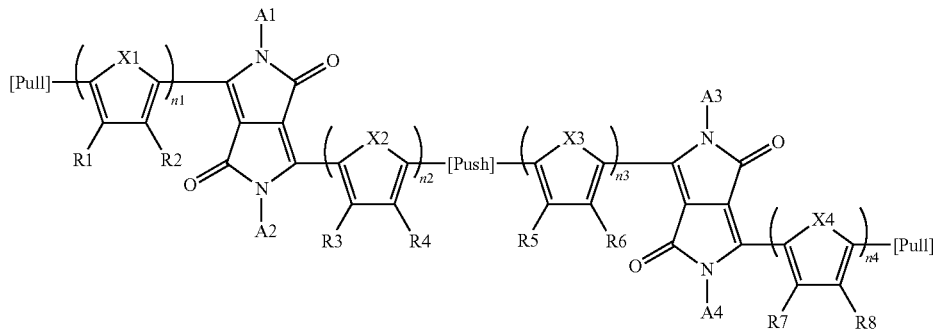

In Chemical Formula 1,
n1 to n4 are each an integer from 1 to 3,
when n1 to n4 are each 2 or more, two or more structures in the parenthesis are the same as or different from each other,
[Push] is any one of the following structures,

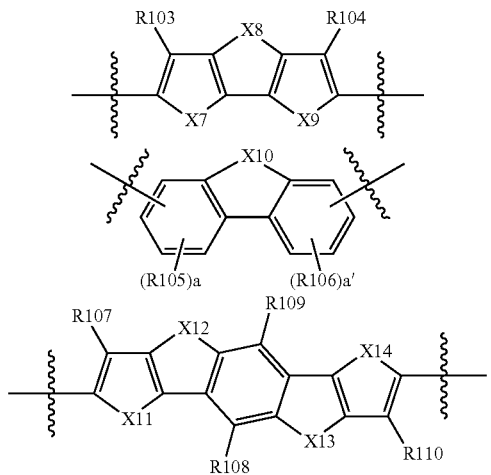

in the structures,
a and a' are each an integer from 1 to 3,
when a is 2 or more, two or more R105's are the same as or different from each other, when a' is 2 or more, two or more R106's are the same as or different from each other, X7 to X14 are the same as or different from each other, and are each independently $CR_aR_b$, $C=CR_aR_b$, $NR_a$, O, $SiR_aR_b$, $PR_a$, S, $GeR_aR_b$, Se, or Te, $R_a$, $R_b$, $R_c$, and R103 to R110 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group,

[Pull]'s are the same as or different from each other, and are any one of the following structures,

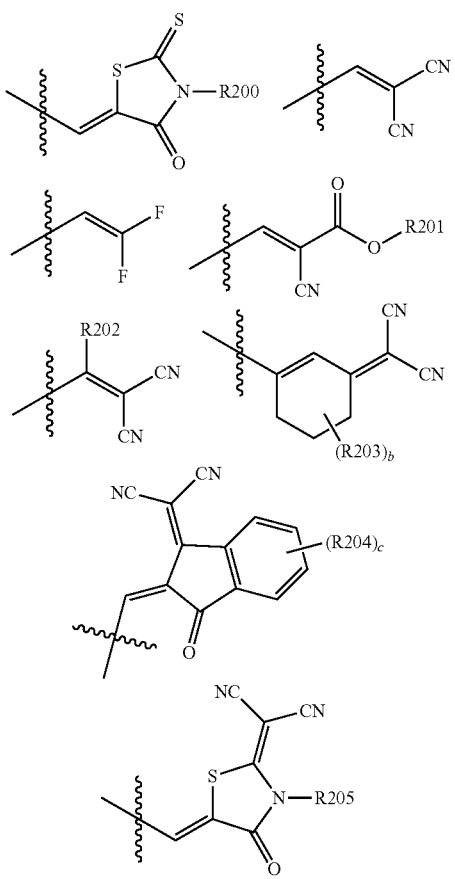

in the structures, b is an integer from 1 to 7, c is an integer from 1 to 4, when b and c are each 2 or more, two or more structures in the parenthesis are the same as or different from each other, R200 to R205 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, X1 to X4 are the same as or different from each other, and are each independently CRR', NR, O, SiRR', PR, S, GeRR', Se, or Te, R, R', R", and R1 to R8 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, A1 to A4 are the same as or different from each other, and are each independently represented by the following Chemical Formula 2,

[Chemical Formula 2]

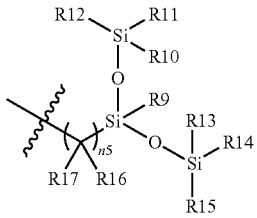

in Chemical Formula 2, n5 is an integer from 0 to 5, when n5 is 2 or more, two or more structures in the parenthesis are the same as or different from each other, R9 to R17 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, and

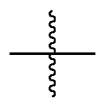

is a moiety bonded to Chemical Formula 1.

Further, the present specification provides an organic solar cell including: a first electrode; a second electrode which is disposed to face the first electrode; and an organic material layer having one or more layers which is disposed between the first electrode and the second electrode and comprises a photoactive layer, in which one or more layers of the organic material layer include the above-described heterocyclic compound.

Advantageous Effects

A heterocyclic compound according to an exemplary embodiment of the present specification includes a [Push] structure having electron donor properties and a [Pull] structure having electron acceptor properties. Further, the heterocyclic compound may include a linker which links the [Push] and the [Pull] having excellent planarity, and allow formed excitons to rapidly move in the molecule, thereby maximizing polarization of the excitons, and may have low band gap characteristics.

In addition, since the heterocyclic compound according to an exemplary embodiment of the present specification includes the structure of Chemical Formula 2, which is a bulky side chain, the solubility may be improved, and it is possible to suppress the heterocyclic compound from aggregating by reducing the interaction between the heterocyclic compounds, and for this reason, when an a bulk-heterojunction film are formed by using acceptor material and Chemical Formula 1 including Chemical Formula 2 as a donor, it is possible to suppress the size of the donor from increasing.

Furthermore, since the heterocyclic compound according to an exemplary embodiment of the present specification includes the structure of Chemical Formula 2, it is possible to impart elasticity to the compound.

Accordingly, the heterocyclic compound may be used as a material for an organic material layer of an organic solar cell, and an organic solar cell including the same may exhibit characteristics which are excellent in an increase in open-circuit voltage and short-circuit current and/or an increase in efficiency, and the like.

The heterocyclic compound according to an exemplary embodiment of the present specification may be used either alone or in mixture with other materials in an organic solar cell, and may be expected to improve the service life of a device by characteristics such as thermal stability of the compound and the increase in efficiency.

BRIEF DESCRIPTION OF DRAWINGS

FIG. 1 is a view illustrating an organic solar cell according to an exemplary embodiment of the present specification.

FIG. 2 is a view illustrating an MS spectrum of Compound 1-b.

FIG. 3 is a view illustrating an MS spectrum of Compound 1-c.

FIG. 4 is a view illustrating an NMR spectrum of Compound 1-c.

FIG. 5 is a view illustrating an MS spectrum of Compound A.

FIG. 6 is a view illustrating an NMR spectrum of Compound A.

FIG. 7 is a view illustrating an MS spectrum of Compound B.

FIG. 8 is a view illustrating an NMR spectrum of Compound B.

FIG. 9 is a view illustrating an MS spectrum of Compound 1.

FIG. 10 is a view illustrating an NMR spectrum of Compound 1.

FIG. 11 is a view illustrating an MS spectrum of Compound 2.

FIG. 12 is a view illustrating the current density according to the voltage in an organic solar cell according to Experimental Example 1.

FIG. 13 is a view illustrating an NMR spectrum of Compound C.

FIG. 14 is a view illustrating an MS spectrum of Compound 3.

101: Substrate
102: First electrode
103: Hole transporting layer
104: Photoactive layer
105: Second electrode

BEST MODE

Hereinafter, the present specification will be described in detail.

An exemplary embodiment of the present specification provides the heterocyclic compound represented by Chemical Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a boron group; an amine group; an arylphosphine group; a phosphine oxide group; an aryl group; and a heterocyclic group, or being substituted with a substituent to which two or more substituents among the exemplified substituents are linked or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a bonding portion.

In the present specification, a halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

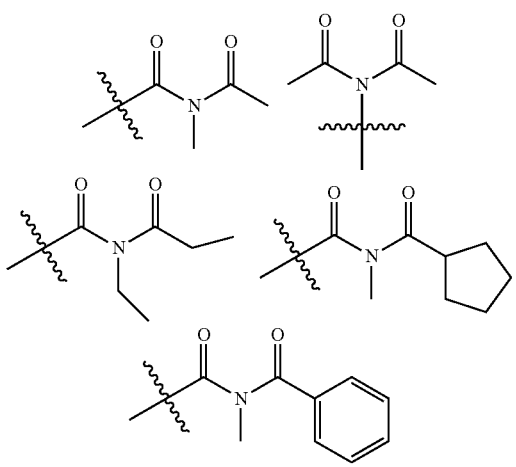

In the present specification, for an amide group, the nitrogen of the amide group may be substituted with hydrogen, a straight, branched, or cyclic alkyl group having 1 to 30 carbon atoms, or an aryl group having 6 to 30 carbon atoms. Specifically, the amide group may be a compound having the following structural formulae, but is not limited thereto.

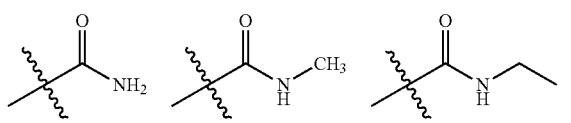

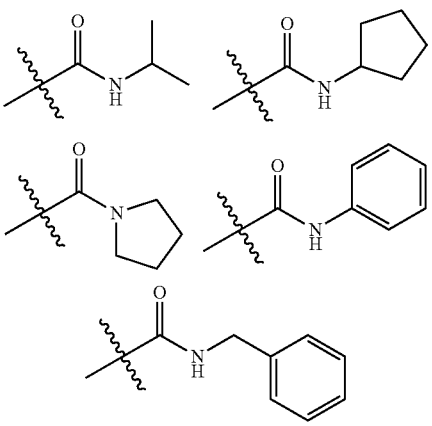

In the present specification, the number of carbon atoms of a carbonyl group is not particularly limited, but is preferably 1 to 30. Specifically, the carbonyl group may be a compound having the following structures, but is not limited thereto.

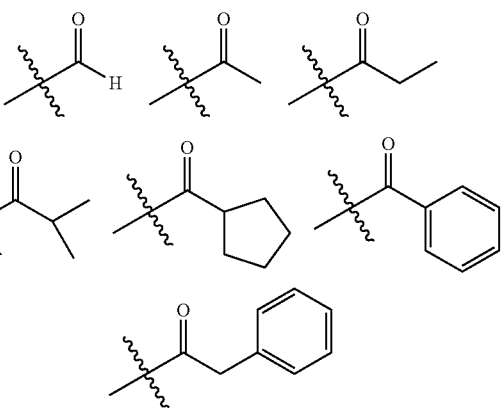

In the present specification, for an ester group, the oxygen of the ester group may be substituted with a straight, branched, or cyclic alkyl group having 1 to 25 carbon atoms, or an aryl group having 6 to 30 carbon atoms. Specifically, the ester group may be a compound having the following structural formulae, but is not limited thereto.

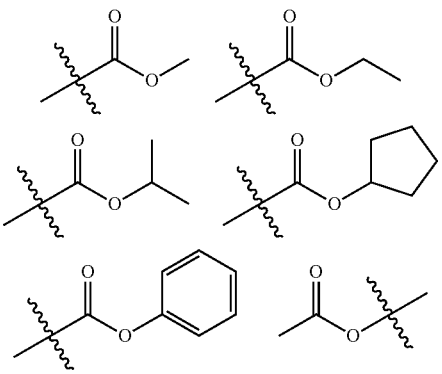

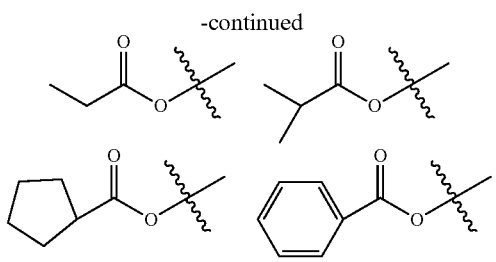

In the present specification, the alkyl group may be straight or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of —$NH_2$; an alkylamine group; an N-arylalkylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, and the like, but are not limited thereto.

In the present specification, an N-alkylarylamineamine group means an amine group in which an alkyl group and an aryl group are substituted with N of the amine group.

In the present specification, an N-arylheteroarylamine group means an amine group in which an aryl group and a heteroaryl group are substituted with N of the amine group.

In the present specification, an N-alkylheteroarylamine group means an amine group in which an alkyl group and a heteroarylamine group are substituted with N of the amine group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, the alkenyl group may be straight or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be —$BR_{100}R_{101}$, and $R_{100}$ and $R_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, dinaphthylphosphine oxide, and the like, but are not limited thereto.

In the present specification, an aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the fluorenyl group may be

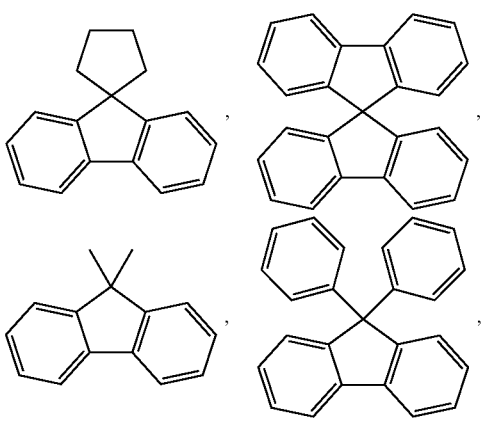

and the like. However, the fluorenyl group is not limited thereto.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, a heteroaryl group includes one or more atoms other than carbon, that is, one or more heteroatoms, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of a heterocyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benz- imidazolyl group, a benzothiazolyl group, a benzocarbazolyl group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, the heterocyclic group may be monocyclic or polycyclic, may be an aromatic ring, an aliphatic ring, or a fused ring of the aromatic ring and the aliphatic ring, and may be selected from the examples of the heteroaryl group.

According to an exemplary embodiment of the present specification, in Chemical Formula 1, [Push] acts as an electron donor in the heterocyclic compound.

According to an exemplary embodiment of the present specification, in Chemical Formula 1, [Pull] acts as an electron acceptor in the heterocyclic compound.

According to an exemplary embodiment of the present specification, in Chemical Formula 1, [Push] has oxidation characteristics in the heterocyclic compound.

According to an exemplary embodiment of the present specification, in Chemical Formula 1, [Pull] has reduction characteristics in the heterocyclic compound.

According to an exemplary embodiment of the present specification, when the [Push] and the [Pull] are measured by using cyclic voltammetry (CV), the [Push] relatively has oxidation characteristics as compared to the [pull], and the [pull] relatively has reduction characteristics as compared to the [Pull].

However, in the present specification, the oxidation characteristics and the reduction characteristics are relative, and the [Push] has oxidation characteristics, but may also have reduction characteristics, and the [Pull] has reduction characteristics, but may also have oxidation characteristics.

In the heterocyclic compound according to an exemplary embodiment of the present specification, [Push] relatively acts as an electron donor, and [Pull] acts as an electron acceptor. In this case, electrons in the lowest unoccupied molecular orbital (LUMO) state are relatively localized in [Pull]. This allows a polarization to be present between [Push] and [Pull].

The present specification may maximize localization of electrons by introducing a linker, which has relatively excellent planarity and has a conjugation, between the [Push] and [Pull], to allow electrons to rapidly move in the direction of [Pull] in the compound. In this case, the formed excitons may rapidly move in the molecule, and polarization of the excitons may be maximized, thereby having low band gap characteristics.

In the present specification, the energy level means the size of energy. Accordingly, even when the energy level is expressed in the negative (−) direction from the vacuum level, it is interpreted that the energy level means an absolute value of the corresponding energy value. For example, the HOMO energy level means the distance from the vacuum level to the highest occupied molecular orbital. Further, the LUMO energy level means the distance from the vacuum level to the lowest unoccupied molecular orbital.

In addition, since the heterocyclic compound according to an exemplary embodiment of the present specification includes the structure represented by Chemical Formula 2, which is a bulky side chain, the solubility may be improved.

Furthermore, since the heterocyclic compound according to an exemplary embodiment of the present specification includes the structure represented by Chemical Formula 2, which is a bulky side chain, it is possible to suppress the heterocyclic compound from aggregating by reducing the interaction between the backbones of an electron donor material in a device, and for this reason, when a bulk heterojunction film are formed by using an acceptor material and Chemical Formula 1 including Chemical Formula 2 as a donor, it is possible to suppress the size of the donor from increasing.

Further, since the heterocyclic compound according to an exemplary embodiment of the present specification includes the structure of Chemical Formula 2, it is possible to impart elasticity to the compound. In this case, the heterocyclic compound may be used as a material for a flexible device.

Accordingly, high current and high efficiency may be expected in a device such as an organic solar cell including the heterocyclic compound according to an exemplary embodiment of the present specification.

According to an exemplary embodiment of the present specification, in Chemical Formula 2, n5 is 5.

According to an exemplary embodiment of the present specification, in Chemical Formula 2, R9 to R15 are the same as or different from each other, and are each independently a substituted or unsubstituted alkyl group.

According to an exemplary embodiment of the present specification, R9 to R15 are the same as or different from each other, and are each independently a substituted or unsubstituted straight or branched alkyl group having 1 to 30 carbon atoms.

According to an exemplary embodiment of the present specification, R9 to R15 are the same as or different from each other, and are each independently a substituted or unsubstituted straight or branched alkyl group having 1 to 20 carbon atoms.

According to an exemplary embodiment of the present specification, R9 to R15 are the same as or different from each other, and are each independently a substituted or unsubstituted straight or branched alkyl group having 1 to 10 carbon atoms.

According to an exemplary embodiment of the present specification, R9 to R15 are the same as or different from each other, and are each independently a substituted or unsubstituted straight or branched alkyl group having 1 to 5 carbon atoms.

According to an exemplary embodiment of the present specification, R9 to R15 are the same as or different from each other, and are each independently a substituted or unsubstituted methyl group.

According to an exemplary embodiment of the present specification, R9 is a methyl group.

According to an exemplary embodiment of the present specification, R10 is a methyl group.

According to an exemplary embodiment of the present specification, R11 is a methyl group.

According to an exemplary embodiment of the present specification, R12 is a methyl group.

According to an exemplary embodiment of the present specification, R13 is a methyl group.

According to an exemplary embodiment of the present specification, R14 is a methyl group.

According to an exemplary embodiment of the present specification, R15 is a methyl group.

According to an exemplary embodiment of the present specification, in Chemical Formula 2, R16 and R17 are hydrogen.

According to an exemplary embodiment of the present specification, the [Push] includes one or two or more from the group consisting of a substituted or unsubstituted arylene group; and a substituted or unsubstituted divalent heterocyclic group including one or more of N, O, S, Si, and Ge.

According to an exemplary embodiment of the present specification, the [Push] includes one or two or more from the group consisting of a substituted or unsubstituted arylene group having 6 to 30 carbon atoms; and a substituted or unsubstituted divalent heterocyclic group having 2 to 30 carbon atoms, which includes one or more of N, O, S, Si, and Ge.

According to an exemplary embodiment of the present specification, the [Push] is any one of the following structures.

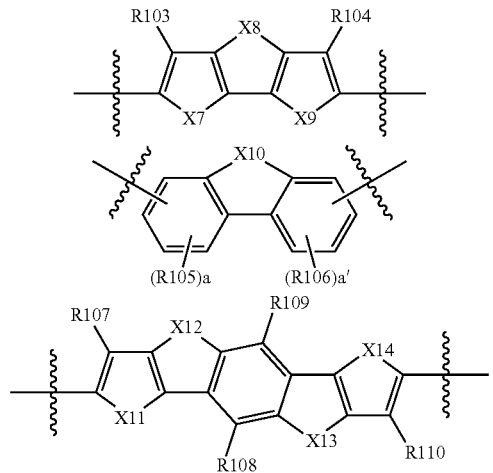

In the structures, a and a' are each an integer from 1 to 3, when a is 2 or more, two or more R105's are the same as or different from each other, when a' is 2 or more, two or more R106's are the same as or different from each other, X7 to X14 are the same as or different from each other, and are each independently $CR_aR_b$, $C=CR_aR_b$, $NR_a$, O, $SiR_aR_b$, $PR_a$, S, $GeR_aR_b$, Se, or Te, $R_a$, $R_b$, $R_c$, and R103 to R110 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, and

is a moiety bonded to Chemical Formula 1.

According to an exemplary embodiment of the present specification, in Chemical Formula 1, [Push] is

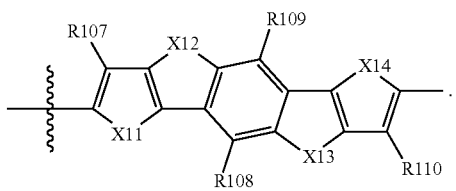

According to an exemplary embodiment of the present specification, in Chemical Formula 1, [Pull] is a substituted or unsubstituted alkenyl group having 2 to 30 carbon atoms.

According to an exemplary embodiment of the present specification, the [Pull] is any one of the following structures.

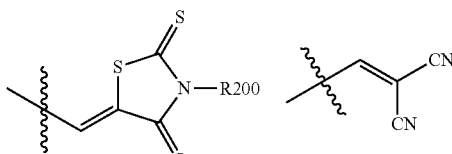

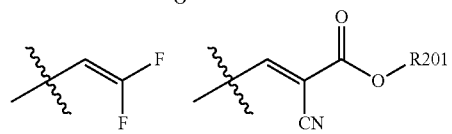

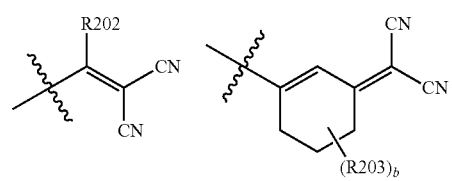

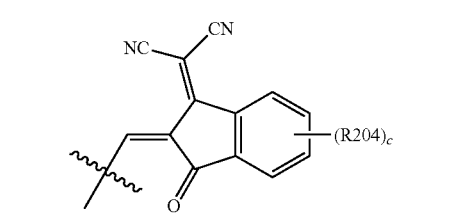

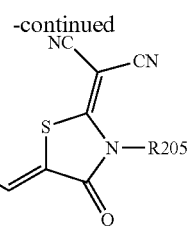

In the structures, b is an integer from 1 to 7, c is an integer from 1 to 4, when b and c are each 2 or more, two or more structures in the parenthesis are the same as or different from each other, R200 to R205 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, and

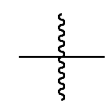

is a moiety bonded to Chemical Formula 1.

According to an exemplary embodiment of the present specification, in Chemical Formula 1, [Pull] is

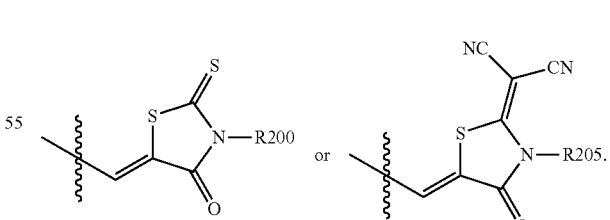

According to an exemplary embodiment of the present specification, the heterocyclic compound represented by Chemical Formula 1 may be represented by the following Chemical Formula 1-1.

[Chemical Formula 1-1]

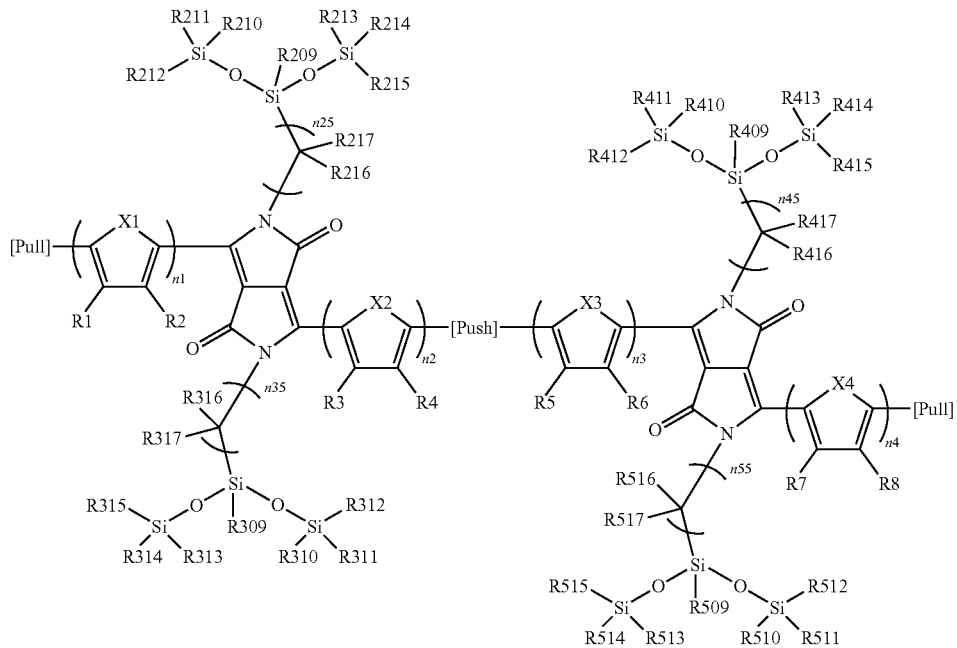

In Chemical Formula 1-1, the definitions of n1 to n4, [Push], [Pull], X1 to X4, and R1 to R8 are the same as those in Chemical Formula 1, n25, n35, n45, and n55 are each an integer from 0 to 5, when n25, n35, n45, and n55 are each 2 or more, two or more structures in the parenthesis are the same as or different from each other, and R209 to R217, R309 to R317, R409 to R417, and R509 to R517 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group.

According to an exemplary embodiment of the present specification, in Chemical Formula 1-1, R209 to R217, R309 to R317, R409 to R417, and R509 to R517 are the same as or different from each other, and are each independently a substituted or unsubstituted alkyl group.

According to an exemplary embodiment of the present specification, R209 to R217, R309 to R317, R409 to R417, and R509 to R517 are the same as or different from each other, and are each independently a substituted or unsubstituted straight or branched alkyl group having 1 to 30 carbon atoms.

According to an exemplary embodiment of the present specification, R209 to R217, R309 to R317, R409 to R417, and R509 to R517 are the same as or different from each other, and are each independently a substituted or unsubstituted straight or branched alkyl group having 1 to 20 carbon atoms.

According to an exemplary embodiment of the present specification, R209 to R217, R309 to R317, R409 to R417, and R509 to R517 are the same as or different from each other, and are each independently a substituted or unsubstituted straight or branched alkyl group having 1 to 10 carbon atoms.

According to an exemplary embodiment of the present specification, R209 to R217, R309 to R317, R409 to R417, and R509 to R517 are the same as or different from each other, and are each independently a substituted or unsubstituted straight alkyl group having 1 to 5 carbon atoms.

According to an exemplary embodiment of the present specification, R209 to R217, R309 to R317, R409 to R417, and R509 to R517 are the same as or different from each other, and are each independently a substituted or unsubstituted methyl group.

According to an exemplary embodiment of the present specification, R209 to R217, R309 to R317, R409 to R417, and R509 to R517 are a methyl group.

According to an exemplary embodiment of the present specification, Chemical Formula 1 may be represented by the following Chemical Formula 1-2.

[Chemical Formula 1-2]

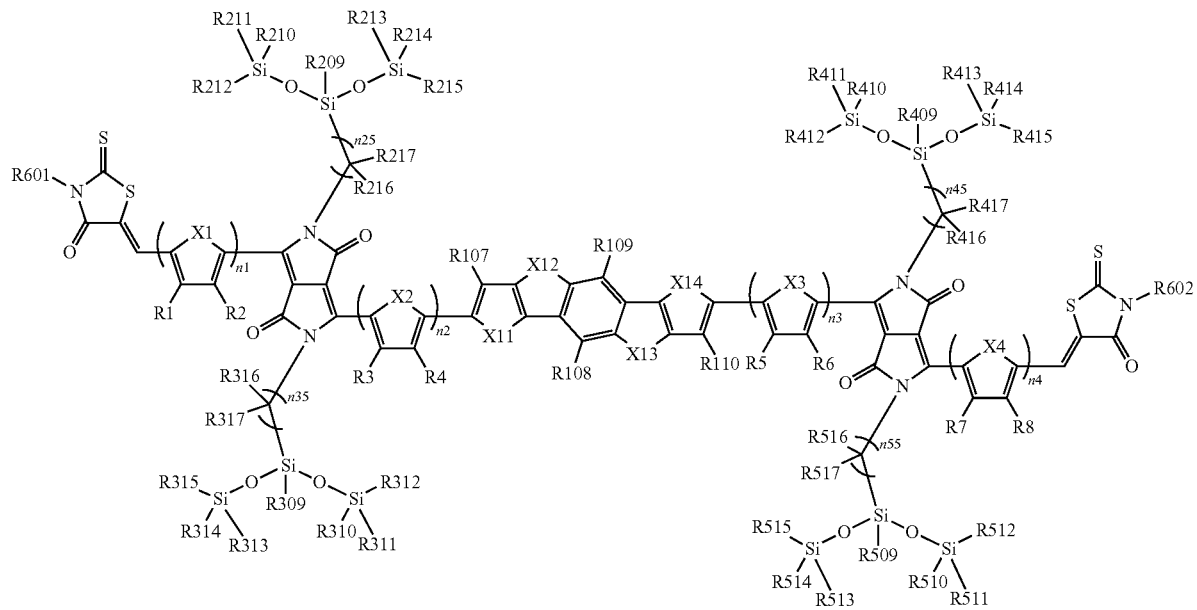

In Chemical Formula 1-2, the definitions of n1 to n4, [Push], [Pull], X1 to X4, and R1 to R8 are the same as those in Chemical Formula 1, the definitions of n25, n35, n45, n55, R209 to R217, R309 to R317, R409 to R417, and R509 to R517 are the same as those in Chemical Formula 1-1, X11 to X14 are the same as or different from each other, and are each independently $CR_aR_b$, $C=CR_aR_b$, $NR_a$, O, $SiR_aR_b$, $PR_a$, S, $GeR_aR_b$, Se, or Te, and $R_a$, $R_b$, $R_c$, R107 to R110, R601, and R602 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group.

According to an exemplary embodiment of the present specification, in Chemical Formula 1-2, X11 to X14 are the same as or different from each other, and are each independently $SiR_aR_b$ or S.

According to an exemplary embodiment of the present specification, in Chemical Formula 1-2, X11 is S.

According to an exemplary embodiment of the present specification, in Chemical Formula 1-2, X12 is $SiR_aR_b$.

According to an exemplary embodiment of the present specification, in Chemical Formula 1-2, X13 is $SiR_aR_b$.

According to an exemplary embodiment of the present specification, in Chemical Formula 1-2, X14 is S.

According to another exemplary embodiment, $R_a$ and $R_b$ are the same as or different from each other, and are each independently a substituted or unsubstituted alkyl group.

According to still another exemplary embodiment, $R_a$ and $R_b$ are the same as or different from each other, and are each independently a substituted or unsubstituted straight or branched alkyl group having 1 to 30 carbon atoms.

According to yet another exemplary embodiment, $R_a$ and $R_b$ are the same as or different from each other, and are each independently a substituted or unsubstituted straight or branched alkyl group having 1 to 10 carbon atoms.

According to still yet another exemplary embodiment, $R_a$ and $R_b$ are the same as or different from each other, and are each independently a substituted or unsubstituted 2-ethylhexyl group.

According to a further exemplary embodiment, $R_a$ and $R_b$ are a 2-ethylhexyl group.

According to another further exemplary embodiment, $R_a$ is a 2-ethylhexyl group.

According to still another further exemplary embodiment, $R_b$ is a 2-ethylhexyl group.

According to an exemplary embodiment of the present specification, in Chemical Formula 1-2, R601 and R602 are the same as or different from each other, and are each independently a substituted or unsubstituted alkyl group.

According to an exemplary embodiment of the present specification, in Chemical Formula 1-2, R601 and R602 are the same as or different from each other, and are each independently a substituted or unsubstituted straight or branched alkyl group having 1 to 30 carbon atoms.

According to an exemplary embodiment of the present specification, in Chemical Formula 1-2, R601 and R602 are the same as or different from each other, and are each independently a substituted or unsubstituted straight or branched alkyl group having 1 to 10 carbon atoms.

According to an exemplary embodiment of the present specification, in Chemical Formula 1-2, R601 and R602 are the same as or different from each other, and are each independently a substituted or unsubstituted n-octyl group.

According to an exemplary embodiment of the present specification, in Chemical Formula 1-2, R601 and R602 are an n-octyl group.

According to an exemplary embodiment of the present specification, in Chemical Formula 1-2, R601 is an n-octyl group.

According to an exemplary embodiment of the present specification, in Chemical Formula 1-2, R602 is an n-octyl group.

According to an exemplary embodiment of the present specification, Chemical Formula 1 may be represented by the following compounds.

group is introduced into each end by bonding the [Push] to each compound are prepared. Thereafter, by introducing [Pull], not only a heterocyclic compound represented by Chemical Formula 1-1, but also a heterocyclic compound represented by Chemical Formula 1 may be prepared.

The heterocyclic compound according to the present specification may be prepared by a multi-step chemical reaction. Monomers are prepared through an alkylation reaction, a Grignard reaction, a Suzuki coupling reaction, a

[Compound 1]

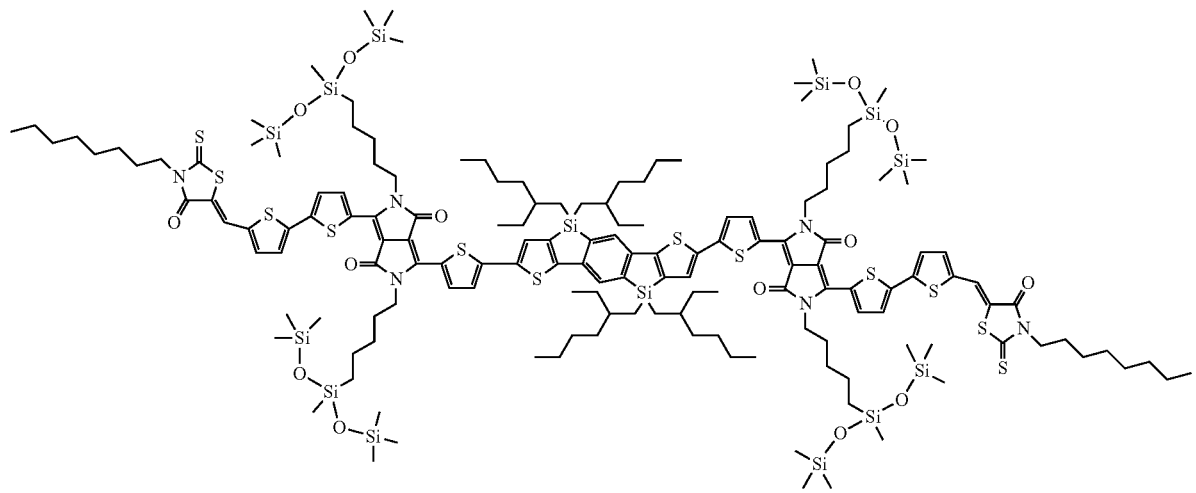

[Compound 2]

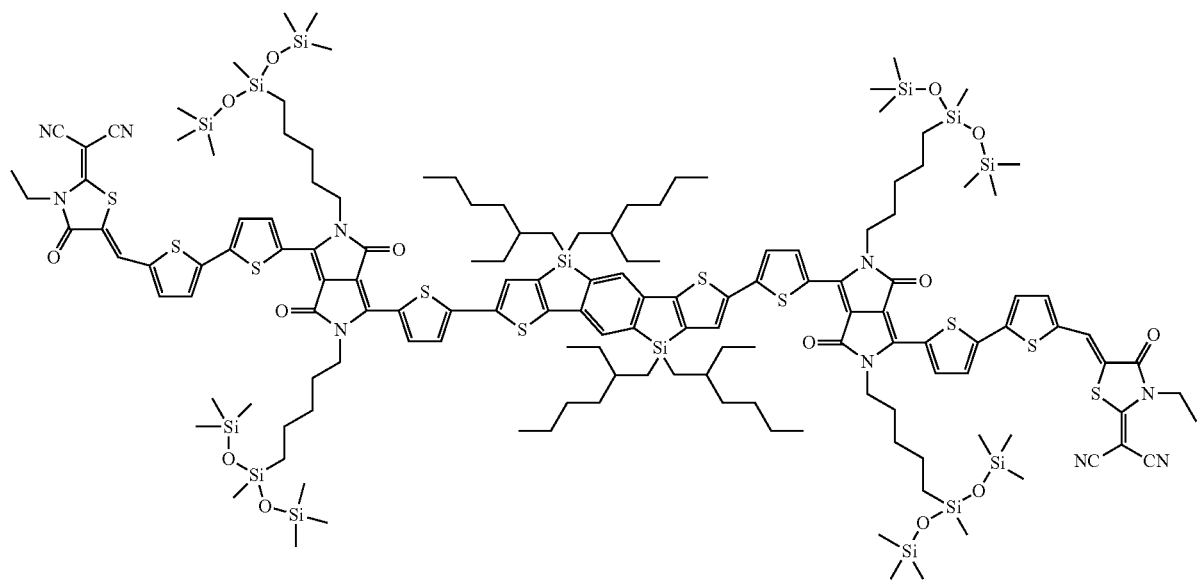

The heterocyclic compound may be prepared based on the Preparation Examples to be described below.

For the heterocyclic compound according to an exemplary embodiment of the present specification, a compound in which an aldehyde group is introduced into the end of a structure in the parenthesis of n1 and a halogen group is introduced into the end of a structure in the parenthesis of n2; a compound in which a halogen group is introduced into the end of a structure in the parenthesis of n3 and an aldehyde group is introduced into the end of a structure in the parenthesis of n4; and a compound in which an aldehyde Stille coupling reaction, and the like, and then final heterocyclic compounds may be prepared through a carbon-carbon coupling reaction such as a Stille coupling reaction. When the substituent to be introduced is a boronic acid or boronic ester compound, the heterocyclic compound may be prepared through a Suzuki coupling reaction, and when the substituent to be introduced is a tributyltin or trimethyltin compound, the heterocyclic compound may be prepared through a Stille coupling reaction, but the method is not limited thereto.

An exemplary embodiment of the present specification provides an organic solar cell including: a first electrode; a second electrode which is disposed to face the first electrode; and an organic material layer having one or more layers which is disposed between the first electrode and the second electrode and comprises a photoactive layer, in which one or more layers of the organic material layer include the heterocyclic compound.

The organic solar cell according to an exemplary embodiment of the present specification includes a first electrode, a photoactive layer, and a second electrode. The organic solar cell may further include a substrate, a hole transporting layer, and/or an electron transporting layer.

In an exemplary embodiment of the present specification, when the organic solar cell accepts a photon from an external light source, an electron and a hole are generated between an electron donor and an electron acceptor. The generated hole is transported to a positive electrode through an electron donor layer.

In an exemplary embodiment of the present specification, the organic material layer includes a hole transporting layer, a hole injection layer, or a layer which simultaneously transports and injects holes, and the hole transporting layer, the hole injection layer, or the layer which simultaneously transports and injects holes includes the heterocyclic compound.

In another exemplary embodiment, the organic material layer includes an electron injection layer, an electron transporting layer, or a layer which simultaneously injects and transports electrons, and the electron injection layer, the electron transporting layer, or the layer which simultaneously injects and transports electrons includes the heterocyclic compound.

FIG. 1 is a view illustrating an organic solar cell according to an exemplary embodiment of the present specification.

In an exemplary embodiment of the present specification, when the organic solar cell accepts a photon from an external light source, an electron and a hole are generated between an electron donor and an electron acceptor. The generated hole is transported to a positive electrode through an electron donor layer.

In an exemplary embodiment of the present specification, the organic solar cell may further include an additional organic material layer. The organic solar cell may reduce the number of organic material layers by using an organic material which simultaneously has various functions.

In an exemplary embodiment of the present specification, the first electrode is an anode, and the second electrode is a cathode. In another exemplary embodiment, the first electrode is a cathode, and the second electrode is an anode.

In an exemplary embodiment of the present specification, in the organic solar cell, a cathode, a photoactive layer, and an anode may be arranged in this order, and an anode, a photoactive layer, and a cathode may be arranged in this order, but the arrangement order is not limited thereto.

In another exemplary embodiment, in the organic solar cell, an anode, a hole transporting layer, a photoactive layer, an electron transporting layer, and a cathode may also be arranged in this order, and a cathode, an electron transporting layer, a photoactive layer, a hole transporting layer, and an anode may also be arranged in this order, but the arrangement order is not limited thereto.

In an exemplary embodiment of the present specification, the organic solar cell has a normal structure. In the normal structure, a substrate, an anode, an organic material layer including a photoactive layer, and a cathode may be stacked in this order.

In an exemplary embodiment of the present specification, the organic solar cell has an inverted structure. In the inverted structure, a substrate, a cathode, an organic material layer including a photoactive layer, and an anode may be stacked in this order.

In an exemplary embodiment of the present specification, the organic solar cell has a tandem structure.

The organic solar cell according to an exemplary embodiment of the present specification may have a photoactive layer having one layer or two or more layers. In the tandem structure, the organic solar sell may include two or more photoactive layers.

In another exemplary embodiment, a buffer layer may be disposed between a photoactive layer and a hole transporting layer, or between a photoactive layer and an electron transporting layer. In this case, a hole injection layer may be further disposed between an anode and a hole transporting layer. Further, an electron injection layer may be further disposed between a cathode and an electron transporting layer.

In an exemplary embodiment of the present specification, the photoactive layer includes one or two or more selected from the group consisting of an electron donor and an electron acceptor, and the electron donor material includes the heterocyclic compound.

In an exemplary embodiment of the present specification, the electron acceptor material may be selected from the group consisting of fullerene, fullerene derivatives, bathocuproine, semi-conducting elements, semi-conducting compounds, and combinations thereof. Specifically, the electron acceptor material is one or two or more compounds selected from the group consisting of fullerene, fullerene derivatives ((6,6)-phenyl-C61-butyric acid-methylester (PCBM) or (6,6)-phenyl-C61-butyric acid-cholesteryl ester (PCBCR)), perylene, polybenzimidazole (PBI), and 3,4,9,10-perylene-tetracarboxylic bis-benzimidazole (PTCBI).

In an exemplary embodiment of the present specification, the electron donor and the electron acceptor constitute a bulk heterojunction (BHJ).

The bulk heterojunction means that an electron donor material and an electron acceptor material are mixed with each other in a photoactive layer.

In an exemplary embodiment of the present specification, the photoactive layer has a bilayer thin film structure including an n-type organic material layer and a p-type organic material layer, and the p-type organic material layer includes the heterocyclic compound.

In the present specification, the substrate may be a glass substrate or a transparent plastic substrate having excellent transparency, surface smoothness, ease of handling, and waterproofing properties, but is not limited thereto, and the substrate is not limited as long as the substrate is typically used in the organic solar cell. Specific examples thereof include glass or polyethylene terephthalate (PET), polyethylene naphthalate (PEN), polypropylene (PP), polyimide (PI), triacetyl cellulose (TAC), and the like, but are not limited thereto.

The anode electrode may be made of a material which is transparent and has excellent conductivity, but is not limited thereto. Examples thereof include a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as $ZnO:Al$ or $SnO_2:Sb$; a conductive polymer such as poly(3-methylthiophene), poly[3,4-(ethylene-1,2-dioxy)thiophene](PEDOT), polypyrrole, and polyaniline; and the like, but are not limited thereto.

A method of forming the anode electrode is not particularly limited, but the anode electrode may be formed, for example, by being applied onto one surface of a substrate using sputtering, e-beam, thermal deposition, spin coating, screen printing, inkjet printing, doctor blade, or a gravure printing method, or by being coated in the form of a film.

When the anode electrode is formed on a substrate, the anode electrode may be subjected to processes of cleaning, removing moisture, and hydrophilic modification.

For example, a patterned ITO substrate is sequentially cleaned with a cleaning agent, acetone, and isopropyl alcohol (IPA), and then dried on a heating plate at 100 to 150° C. for 1 to 30 minutes, preferably at 120° C. for 10 minutes in order to remove moisture, and when the substrate is completely cleaned, the surface of the substrate is hydrophilically modified.

Through the surface modification as described above, the junction surface potential may be maintained at a level suitable for a surface potential of a photoactive layer. Further, during the modification, a polymer thin film may be easily formed on an anode electrode, and the quality of the thin film may also be improved.

Examples of a pre-treatment technology for an anode electrode include a) a surface oxidation method using a parallel flat plate-type discharge, b) a method of oxidizing a surface through ozone produced by using UV rays in a vacuum state, c) an oxidation method using oxygen radicals produced by plasma, and the like.

One of the methods may be selected depending on the state of an anode electrode or a substrate. However, even though any method is used, it is preferred to commonly prevent oxygen from leaving from the surface of the anode electrode or the substrate, and maximally suppress moisture and organic materials from remaining. In this case, it is possible to maximize a substantial effect of the pre-treatment.

As a specific example, it is possible to use a method of oxidizing a surface through ozone produced by using UV. In this case, a patterned ITO substrate after being ultrasonically cleaned is baked on a hot plate and dried well, and then introduced into a chamber, and the patterned ITO substrate may be cleaned by ozone generated by reacting an oxygen gas with UV light by operating a UV lamp.

However, the surface modification method of the patterned ITO substrate in the present specification need not be particularly limited, and any method may be used as long as the method is a method of oxidizing a substrate.

The cathode electrode may be a metal having a low work function, but is not limited thereto. Specific examples thereof include: a metal such as magnesium, calcium, sodium, potassium, titanium, indium, yttrium, lithium, gadolinium, aluminum, silver, tin, and lead, or an alloy thereof; and a multi-layer structured material such as LiF/Al, $LiO_2$/Al, LiF/Fe, Al:Li, Al:$BaF_2$, and Al:$BaF_2$:Ba, but are not limited thereto.

The cathode electrode may be deposited and formed in a thermal deposition apparatus showing a vacuum degree of $5\times10^{-7}$ torr or less, but the forming method is not limited only to this method.

The hole transporting layer and/or electron transporting layer materials serve to efficiently transfer electrons and holes separated from a photoactive layer to an electrode, and the materials are not particularly limited.

Examples of the hole transporting layer material may be poly(3,4-ethylenedioxythiophene) doped with poly(styrene sulfonate) (PEDOT:PSS) and molybdenum oxide ($MoO_x$); vanadium oxide ($V_2O_5$); nickel oxide (NiO); and tungsten oxide ($WO_x$), and the like, but are not limited thereto.

The electron transporting layer material may be electron-extracting metal oxides, and specific examples thereof include: a metal complex of 8-hydroxyquinoline; a complex including $Alq_3$; a metal complex including Liq; LiF; Ca; titanium oxide ($TiO_x$); zinc oxide (ZnO); and cesium carbonate ($Cs_2CO_3$), and the like, but are not limited thereto.

The photoactive layer may be formed by dissolving a photoactive material such as an electron donor and/or an electron acceptor in an organic solvent, and then applying the solution by a method such as spin coating, dip coating, screen printing, spray coating, doctor blade, and brush painting, but the forming method is not limited thereto.

MODE FOR INVENTION

A preparation method of the heterocyclic compound and the manufacture of an organic solar cell including the same will be described in detail in the following Preparation Examples and Examples. However, the following Examples are provided for exemplifying the present specification, and the scope of the present specification is not limited thereby.

Preparation Example 1. Preparation of Compound 1

(1) Preparation of Compound 1-b

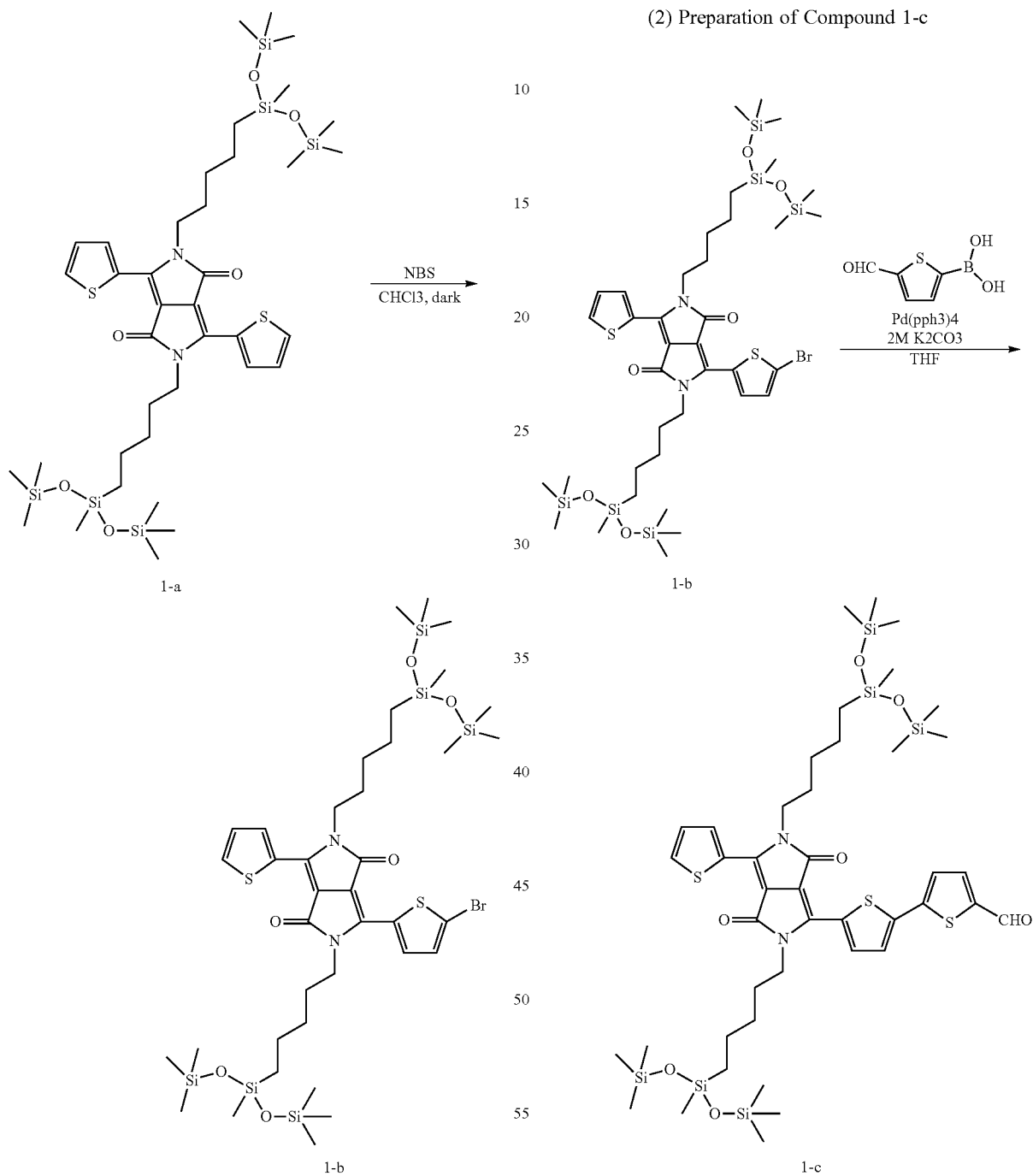

remaining product was purified with silica column (eluent: hexane:dichloromethane=2:1) to obtain black Powder 1-b. (Yield: 71%)

FIG. 2 is a view illustrating an MS spectrum of Compound 1-b.

(2) Preparation of Compound 1-c

After 1-a (5.29 g, 6 mmol) was dissolved in 150 mL of chloroform, N-bromosuccinimide (1.28 g, 7.2 mmol) was injected thereinto at room temperature, and then the resulting mixture was stirred for 48 hours. After reaction, the reactant was added to 250 mL of water, and an extraction was performed with dichloromethane. Thereafter, the remaining water was removed over magnesium sulfate, and the solvent was removed under reduced pressure. The 1-b (4.092 g, 4.26 mmol) and 2-aldehyde-thiophene boronic ester (0.935 g, 6 mmol) were dissolved in 200 mL of tetrahydrofuran and 50 mL of 2 M potassium carbonate, a tetrakis(triphenylphosphine)palladium (0) catalyst (0.2427 g, 0.21 mmol) was added thereto, and the resulting mixture was stirred at 70° C. for 72 hours. After reaction, an extraction was performed with dichloromethane, the remaining water was removed over magnesium sulfate, and then the solvent was removed under reduced pressure. The remaining product was purified with silica column (eluent: hexane:diromethane=10:1 to 1:1) to obtain blackish violet Solid 1-c. (Yield: 79%)

FIG. 3 is a view illustrating an MS spectrum of Compound 1-c.

FIG. 4 is a view illustrating an NMR spectrum of Compound 1-c.

(3) Preparation of Compound A

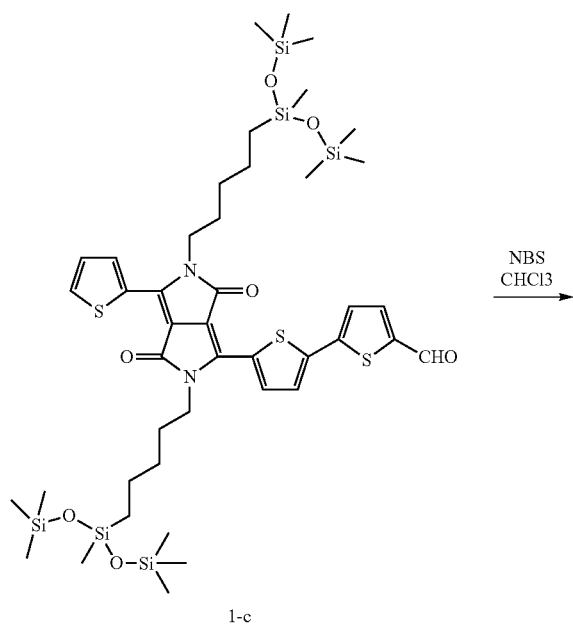

1-c (3 g, 3.03 mmol) was dissolved in 80 mL of chloroform, N-bromosuccinimide (1.28 g, 7.2 mmol) was added thereto, and then the resulting mixture was stirred at room temperature for 48 hours. After reaction, an extraction was performed with dichloromethane, the remaining water was removed over magnesium sulfate, and the solvent was removed under reduced pressure. The remaining product was purified with silica column (eluent: hexane:dichloromethane=10:1 to 1:1) to obtain blackish violet Solid A. (Yield: 81%)

FIG. 5 is a view illustrating an MS spectrum of Compound A.

FIG. 6 is a view illustrating an NMR spectrum of Compound A.

(4) Preparation of Compound B

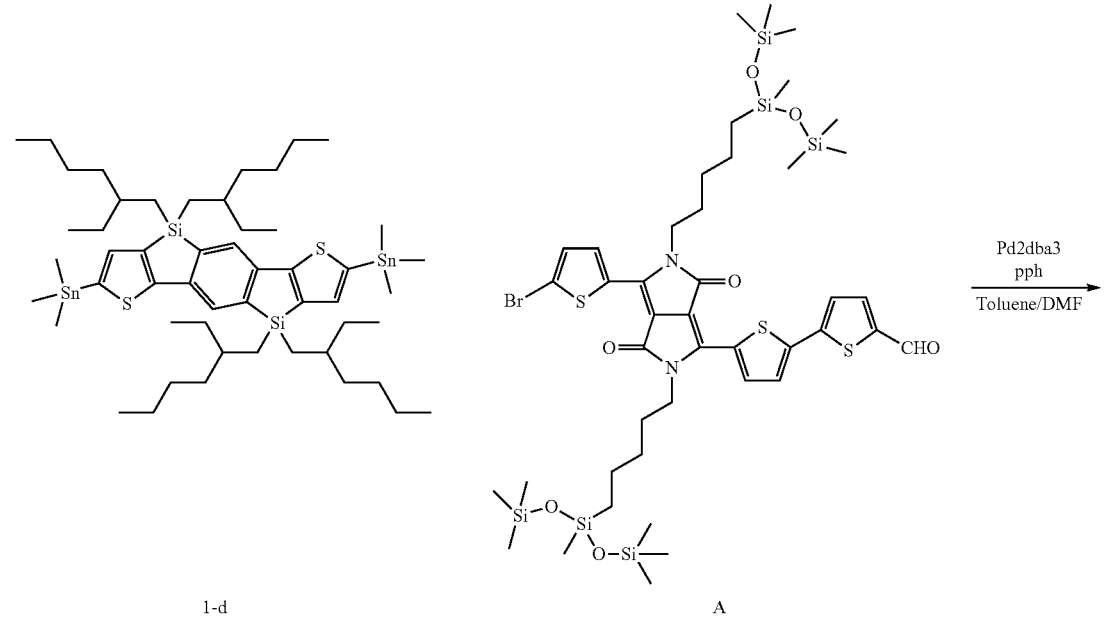

-continued

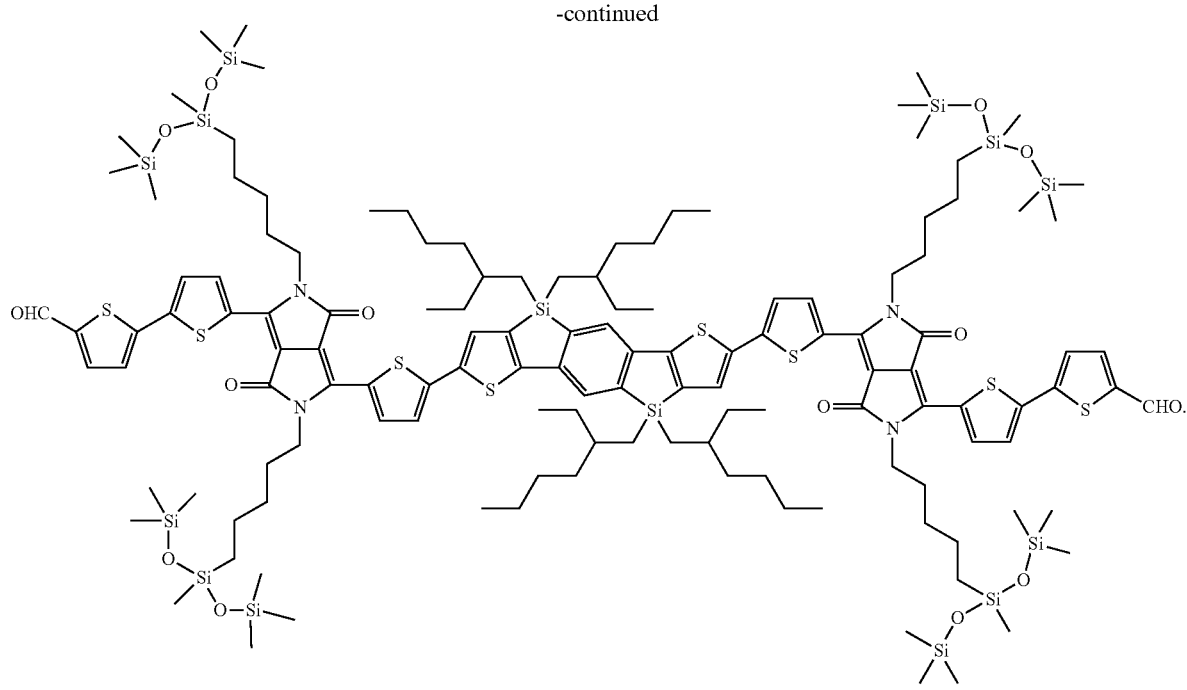

B 1-d (1.18 g, 1.10 mmol) and A (2.623 g, 2.45 mmol) were dissolved in 60 mL of toluene and 6 mL of DMF, a Pd$_2$dba$_3$ catalyst (0.0504 g, 0.055 mmol) and a triphenylphosphine ligand (0.0577 g, 0.22 mmol) were added thereto, and the resulting mixture was stirred at 110° C. for 48 hours. After reaction, an extraction was performed with dichloromethane, the remaining water was removed over magnesium sulfate (MgSO$_4$), and then the solvent was removed under reduced pressure. A dark violet Solid B was obtained by subjecting the remaining product to silica column (eluent: hexane). (Yield: 57%)

FIG. 7 is a view illustrating an MS spectrum of Compound B.

FIG. 8 is a view illustrating an NMR spectrum of Compound B.

(5) Preparation of Compound 1

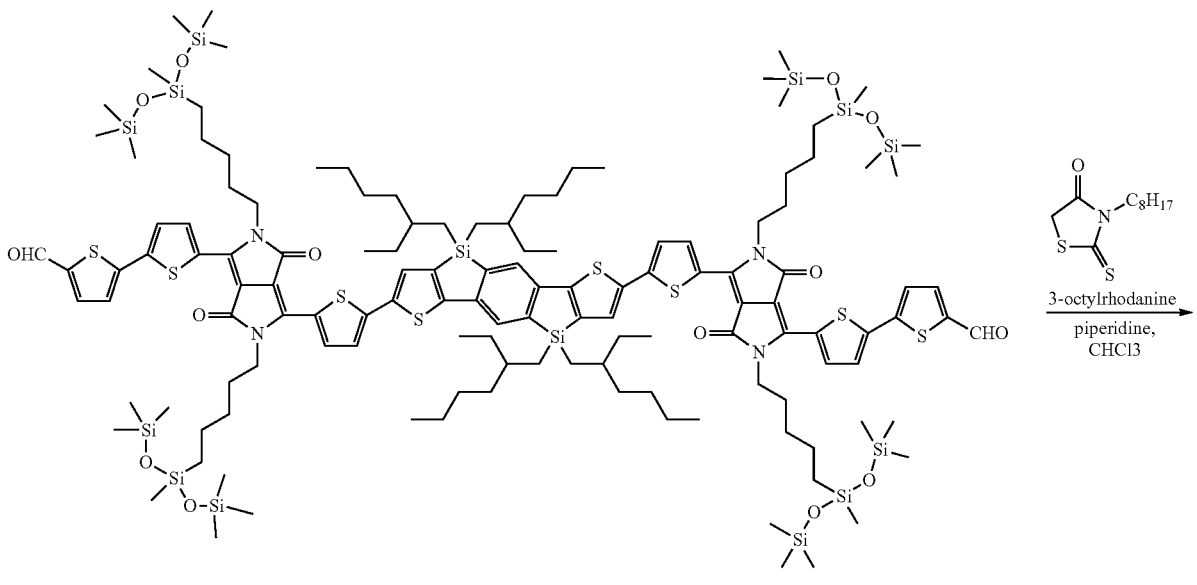

B

-continued

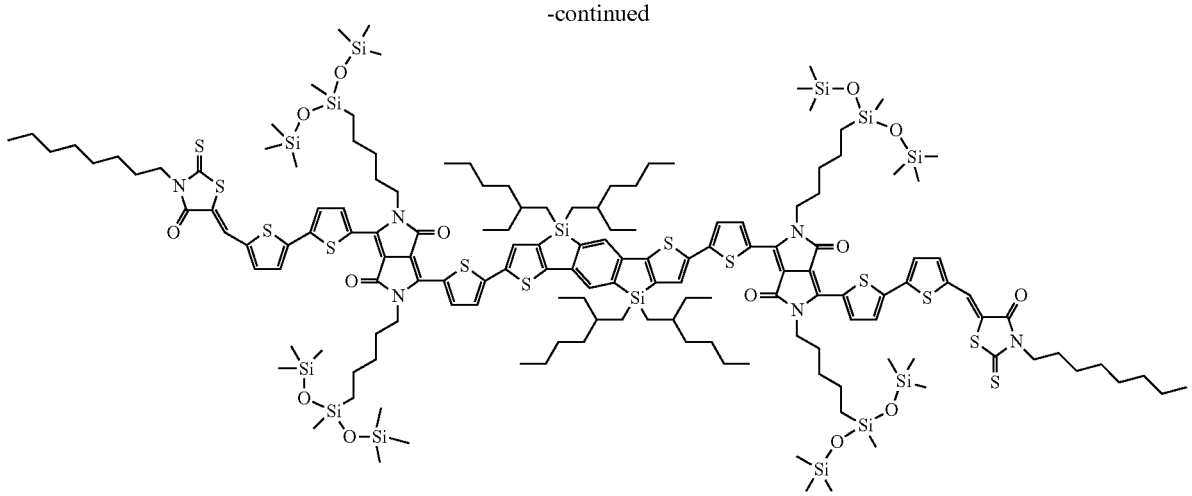

Compound 1

B (409 g, 015 mmol) and 3-octylrhodanine (0.3681 g, 1.5 mmol) were dissolved in 30 mL of CHCl$_3$, three drops of piperidine were added thereto at room temperature, and the resulting mixture was refluxed for 24 hours. After reaction, an extraction was performed with DCM, the remaining water was removed over magnesium sulfate (MgSO$_4$), and then the solvent was removed under reduced pressure. A dark brown solid was obtained by subjecting the remaining product to silica column (eluent: CH$_2$Cl$_2$ to CHCl$_3$). The obtained solid was recrystallized two or three times with CHCl$_3$ and n-hexane to obtain Compound 1. (Yield: 67%)

FIG. 9 is a view illustrating an MS spectrum of Compound 1.

FIG. 10 is a view illustrating an NMR spectrum of Compound 1.

Preparation Example 2. Preparation of Compound 2

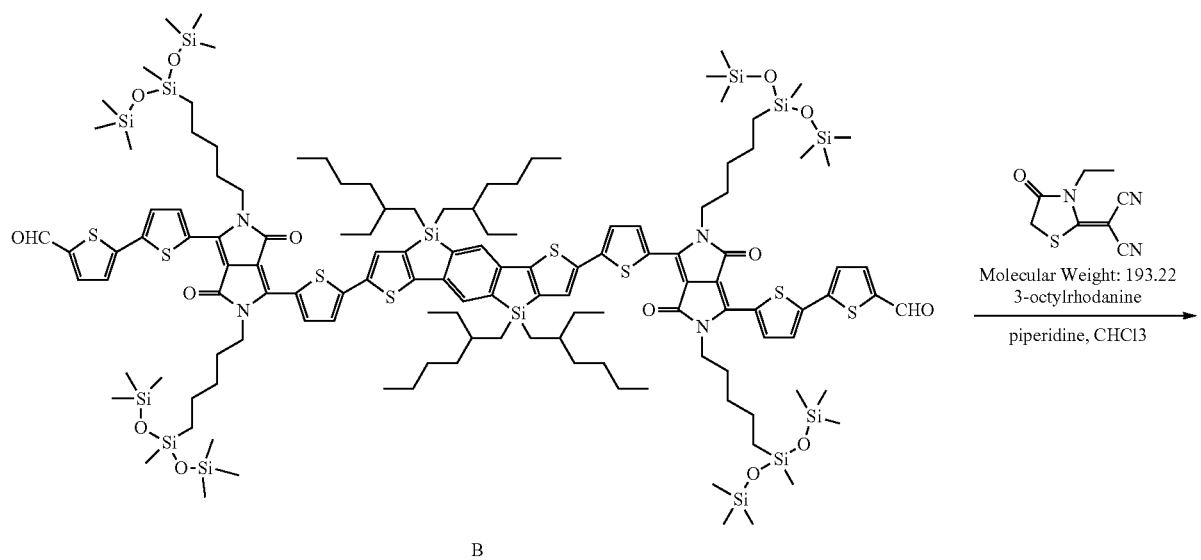

B

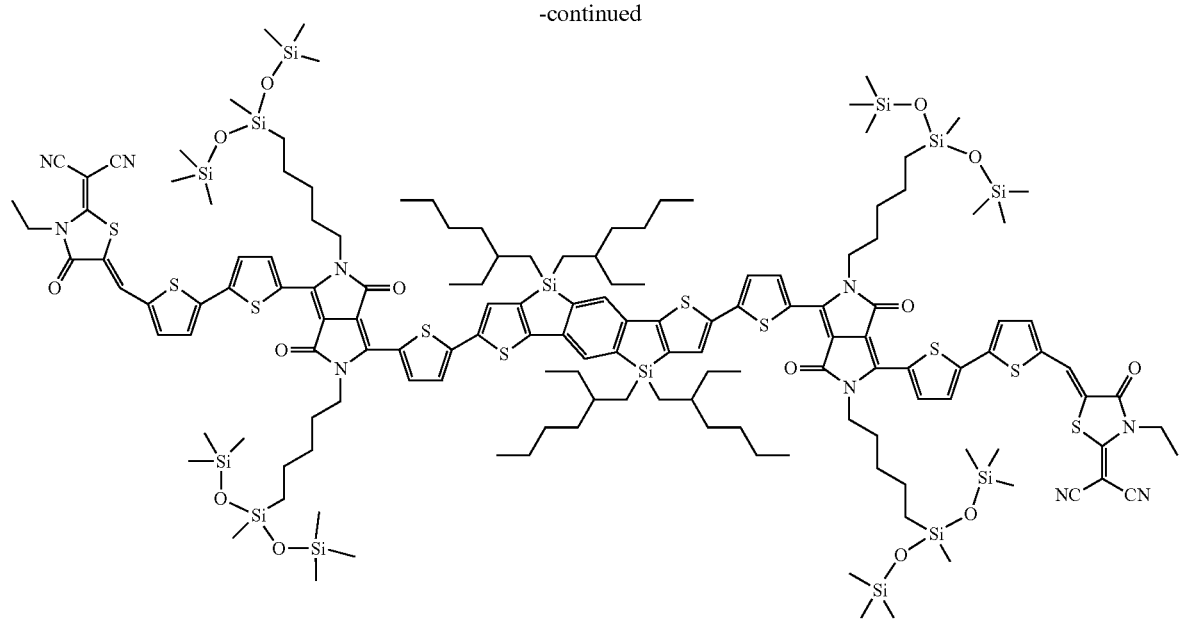
Compound 2
Compound 2 was prepared in the same manner as in the preparation of Compound 1, except that Compound B (1.09 g, 0.4 mmol) and DiCN-rhodanine (0.773 g, 3 mmol) were used for 40 mL of $CHCl_3$ in the preparation of Compound 1. (Yield: 71%)
FIG. 11 is a view illustrating an MS spectrum of Compound 2.
Preparation Example 3. Preparation of Compound 3
(1) Preparation of Compound C
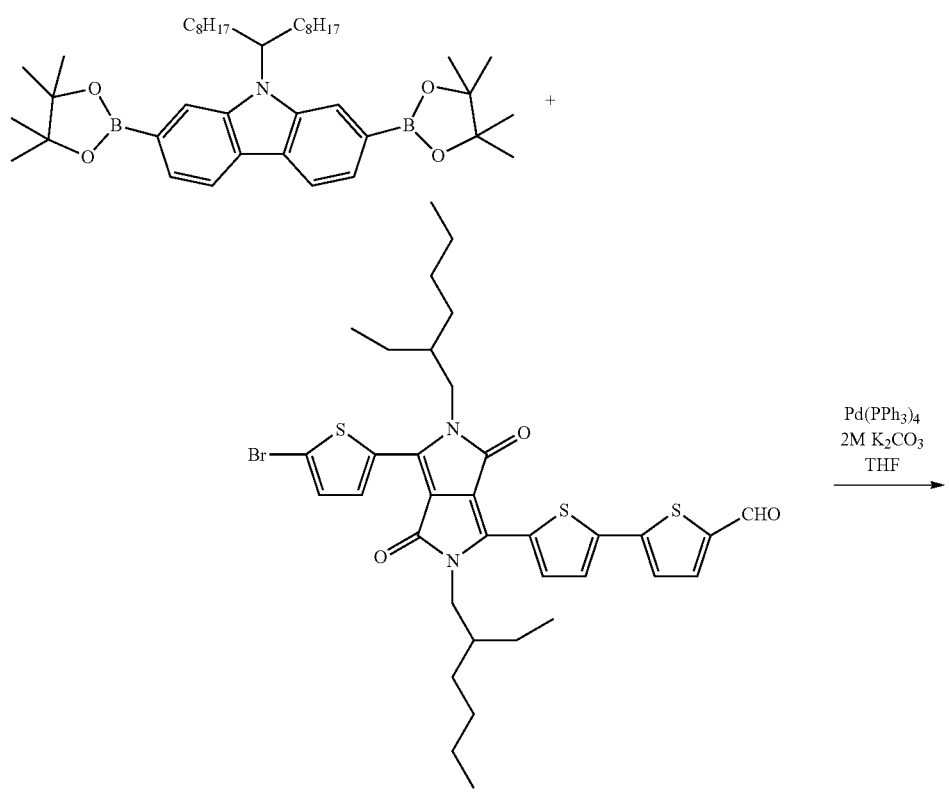

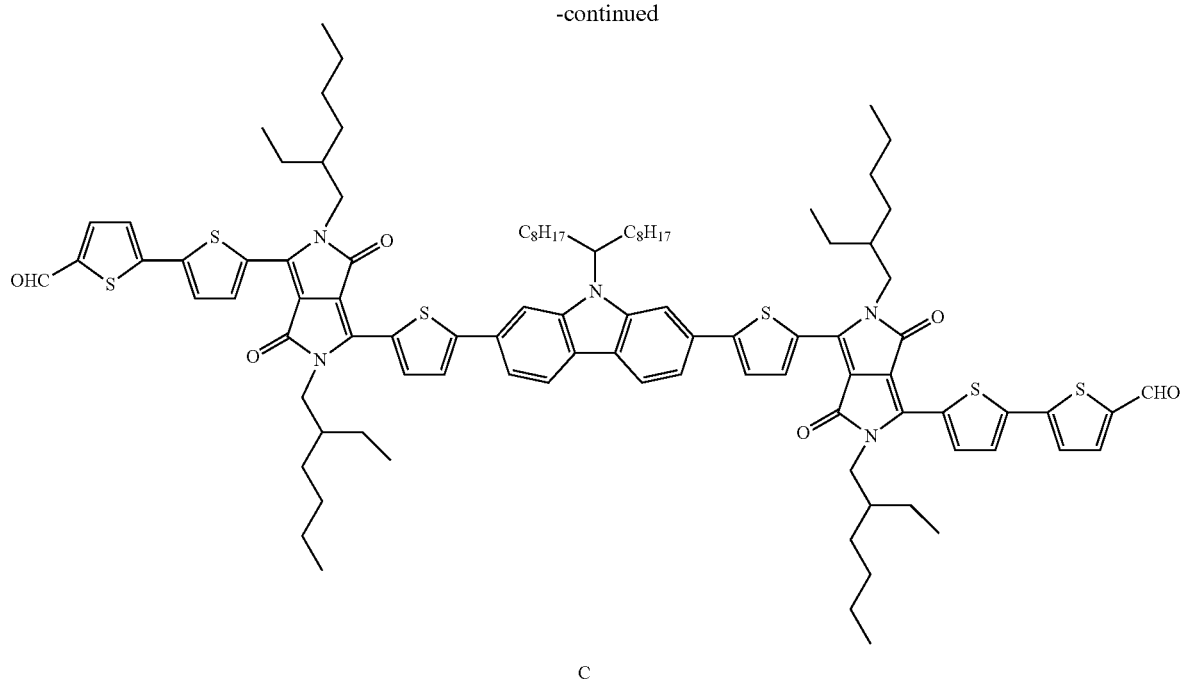

C 9-(heptadecan-9-yl)-2,7-bis(4,4,5,5-tetramethyl-1,3,2-dioxaborolan-2-yl)-9H-carbazole (0.46 g, 0.7 mmol) and 1-e (1.07 g, 1.5 mmol) were dissolved in 30 mL of THF, a tetrakis(triphenylphosphine)palladium(0) (Pd(PPh$_3$)$_4$) catalyst (0.0578 g, 0.05 mmol) was added thereto, and then 7.5 mL of 2 M K$_2$CO$_3$ was added thereto, and the resulting mixture was stirred at 70° C. for 48 hours. After reaction, an extraction was performed with DCM, the remaining water was removed over magnesium sulfate (MgSO$_4$), and then the solvent was removed under reduced pressure. A brown Compound C was obtained by subjecting the remaining product to silica column (eluent: DCM to CHCl$_3$). (Yield: 59%)

FIG. 13 is a view illustrating an NMR spectrum of Compound C.

(2) Preparation of Compound 3

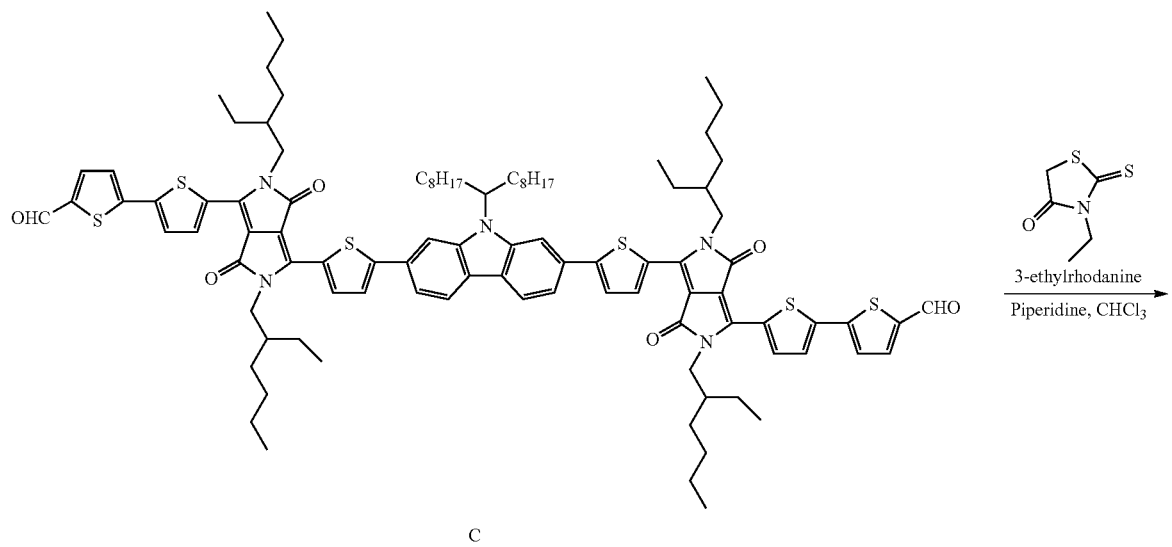

C

-continued

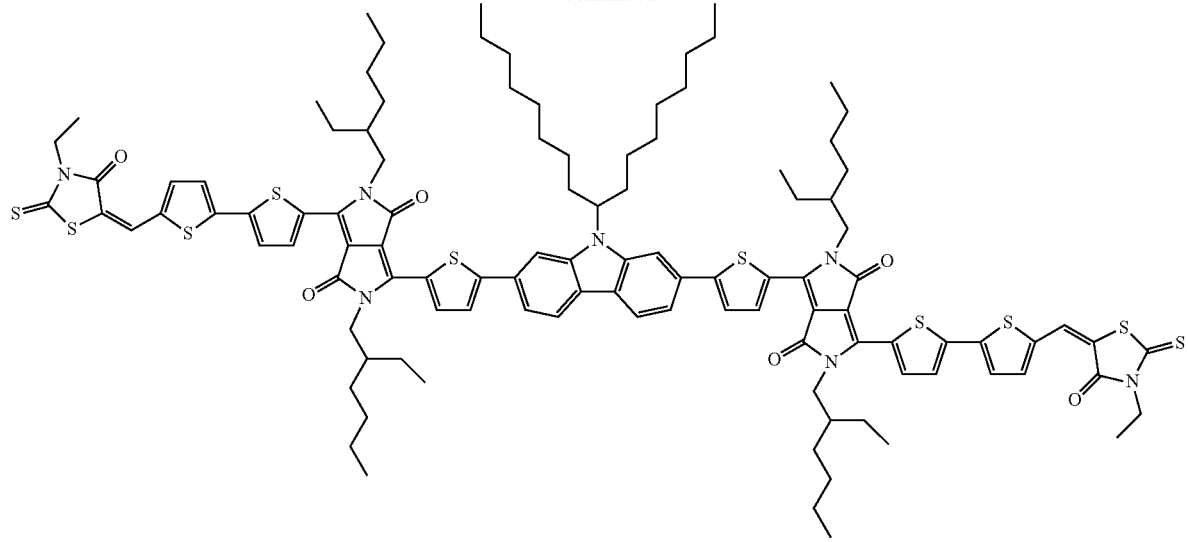

Compound 3

Compound C (0.401 g, 0.24 mmol), three drops of piperidine, and 3-ethylrhodanine (0.743 g, 4.61 mmol) were put into 25 mL of chloroform (CHCl$_3$), and the resulting solution was refluxed under nitrogen for 24 hours. After reaction, the solution was extracted with dichloromethane (DCM), the remaining water was removed over magnesium sulfate (MgSO$_4$), and then the solvent was removed under reduced pressure. Compound 3 being a dark purplish brown solid was obtained by subjecting the remaining product to silica column (eluent: CHCl$_3$:EA gradient).

FIG. 14 is a view illustrating an MS spectrum of Compound 3.

Experimental Example 1. Manufacture of Organic Solar Cell

A composite solution was prepared by dissolving Compound 1 and PC$_{70}$BM at a ratio of 1:1 in chlorobenzene (CB). In this case, the concentration was adjusted to 4 wt %, and the organic solar cell was made to have an inverted structure of ITO/ZnO/a photoactive layer/MoO$_3$/Ag. A glass substrate coated with ITO with 1.5×1.5 cm$^2$ as a bar type was ultrasonically washed by using distilled water, acetone, and 2-propanol, the ITO surface was treated with ozone for 10 minutes, and then a zinc oxide precursor (ZnO precursor solution: ZnO nanoparticle 25 mg/ml in butanol) was produced, the zinc oxide (ZnO) solution was spin-coated at 4,000 rpm for 40 seconds, and then the remaining solvent was removed by performing a heat treatment at 100° C. for 10 minutes, thereby completing an electron transporting layer. For the coating of the photoactive layer, the composite solution of Compound 1 and PC$_{70}$BM was spin-coated at 1,000 rpm for 20 seconds. In a thermal deposition apparatus, MoO$_3$ was deposited to have a thickness of 10 nm at a rate of 0.2 Å/s, thereby manufacturing a hole transporting layer. After the manufacturing in the above order, Ag was deposited to have a thickness of 100 nm at a rate of 1 Å/s in a thermal deposition apparatus, thereby manufacturing an organic solar cell having an inverted structure.

Comparative Example 1. Manufacture of Organic Solar Cell

A composite solution was prepared by dissolving Compound 3 and PC$_{60}$BM at a ratio of 1:2 in chloroform (CF). In this case, the concentration was adjusted to 2 wt %, and the organic solar cell was made to have a structure of ITO/PEDOT:PSS/a photoactive layer/Al. A glass substrate coated with ITO was ultrasonically washed by using distilled water, acetone, and 2-propanol, the ITO surface was treated with ozone for 10 minutes, the PEDOT:PSS(Al4083) was spin-coated at 4,000 rpm for 40 seconds with a thickness of 45 nm, and then heat treatment at 235° C. for 5 minutes. For the coating of the photoactive layer, a compound-PCBM composite solution was filtered with a 0.45 μm PP syringe filter and spin-coated, and then an organic solar cell was manufactured by depositing Al to have a thickness of 100 nm using a thermal evaporator under a vacuum of 3×10$^{-8}$ torr.

The photoelectric conversion characteristics of the organic solar cells manufactured in Experimental Example 1 and Comparative Example 1 were measured under the condition of 100 mW/cm$^2$ (AM 1.5), and the results are shown in the following Table 1.

TABLE 1

|  | Voc (V) | Jsc (mA/cm$^2$) | FF (%) | PCE (%) |
| --- | --- | --- | --- | --- |
| Experimental Example 1 | 0.801 | 9.914 | 57.7 | 4.58 |
| Comparative Example 1 | 0.785 | 4.392 | 70.6 | 2.5 |

FIG. 12 is a view illustrating the current density according to the voltage in an organic solar cell according to Experimental Example 1.

Voc, Jsc, FF, and PCE(η) mean an open-circuit voltage, a short-circuit current, a fill factor, and energy conversion efficiency, respectively. The open-circuit voltage and the short-circuit current are an X axis intercept and a Y axis intercept, respectively, in the fourth quadrant of the voltage-current density curve, and as the two values are increased, the efficiency of the solar cell is preferably increased. In addition, the fill factor is a value obtained by dividing the area of a rectangle, which may be drawn within the curve, by the product of the short-circuit current and the open-circuit voltage. The energy conversion efficiency may be obtained when these three values are divided by the intensity of the irradiated light, and the higher value is preferred. From the results in Table 1, it can be confirmed that the compound according to an exemplary embodiment of the present specification exhibits high efficiency.

The invention claimed is:

1. A heterocyclic compound of Chemical Formula 1-1:

[Chemical Formula 1-1]

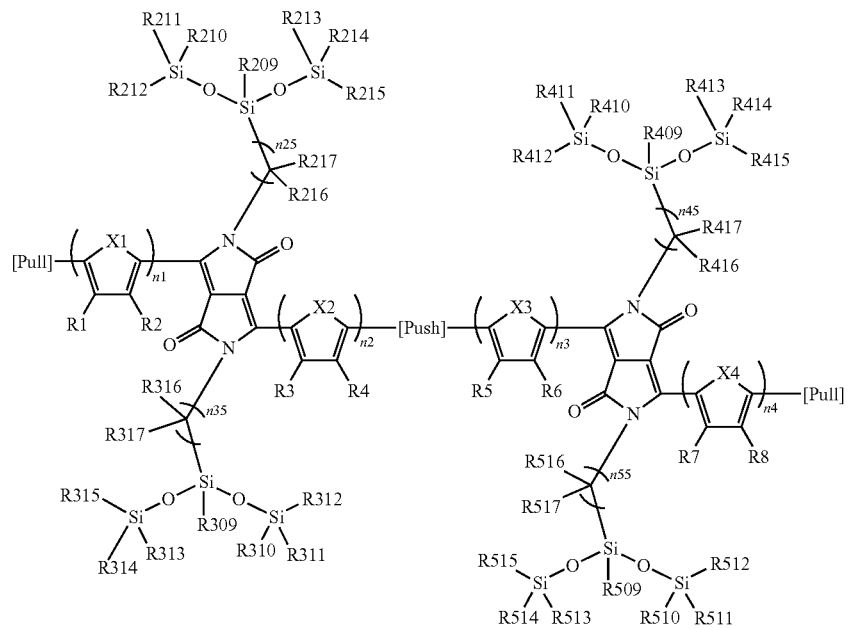

wherein:

n1 and n4 are each 2;

n2 and n3 are each 1;

n25, n35, n45 and n55 are each an integer of from 0 to 5;

X1 to X4 are each S;

R1 to R8, R216, R217, R316, R317, R416, R417, R516 and R517 are each hydrogen;

R209 to R215, R309 to R315, R409 to R415 and R509 to R515 are the same as or different from each other, and are each independently a substituted or unsubstituted alkyl group,

[Push] is

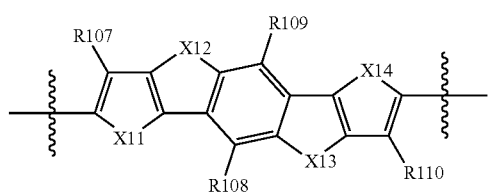

wherein:

X11 and X14 are each S;

X12 and X13 are each SiRaRb;

Ra and Rb are the same as or different from each other, and are each independently a substituted or unsubstituted alkyl group;

R107 to R110 are each hydrogen;

[Pull]s are the same as or different from each other, and are any one of the following structures,

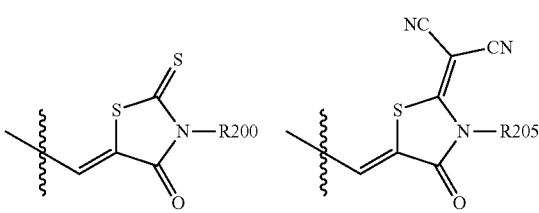

wherein:

R200 and R205 are the same as or different from each other, and are each independently a substituted or unsubstituted alkyl group; and

is a moiety bonded to Chemical Formula 1-1.

2. The heterocyclic compound of claim 1, wherein the compound of Chemical Formula 1-1 is a compound of Chemical Formula 1-2:

[Chemical Formula 1-2]

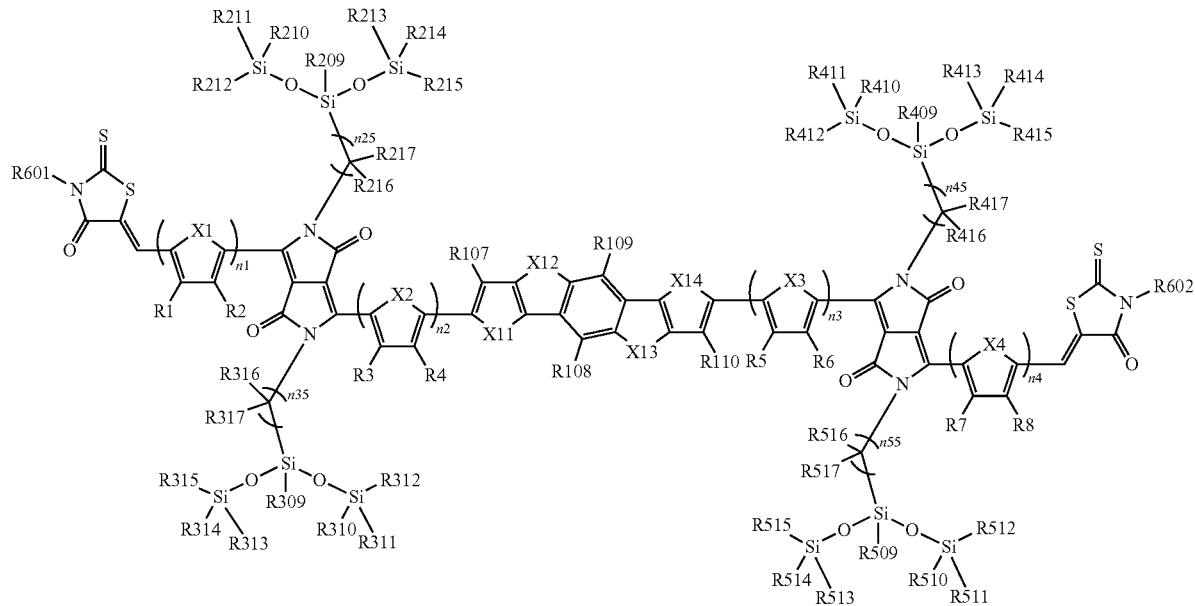

wherein:
the definitions of n1 to n4, n25, n35, n45, n55, X1 to X4, X11 to X14, R107 to R110, R209 to R215, R309 to R315, R409 to R415, R509 to R515, R216, R217, R316, R317, R416, R417, R516, R517 and R1 to R8 are the same as those in Chemical Formula 1-1; and
R601 and R602 are the same as or different from each other, and are each a substituted or unsubstituted alkyl group.

3. The heterocyclic compound of claim 1, wherein the compound of Chemical Formula 1-1 is Compound 1:

[Compound 1]

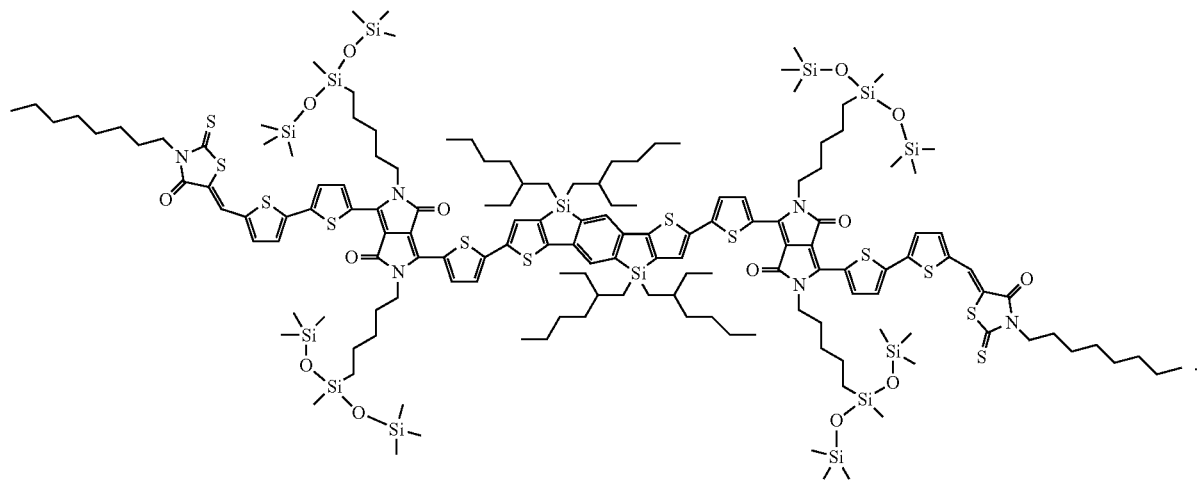

4. The heterocyclic compound of claim 1, wherein the compound of Chemical Formula 1-1 is Compound 2:

[Compound 2]
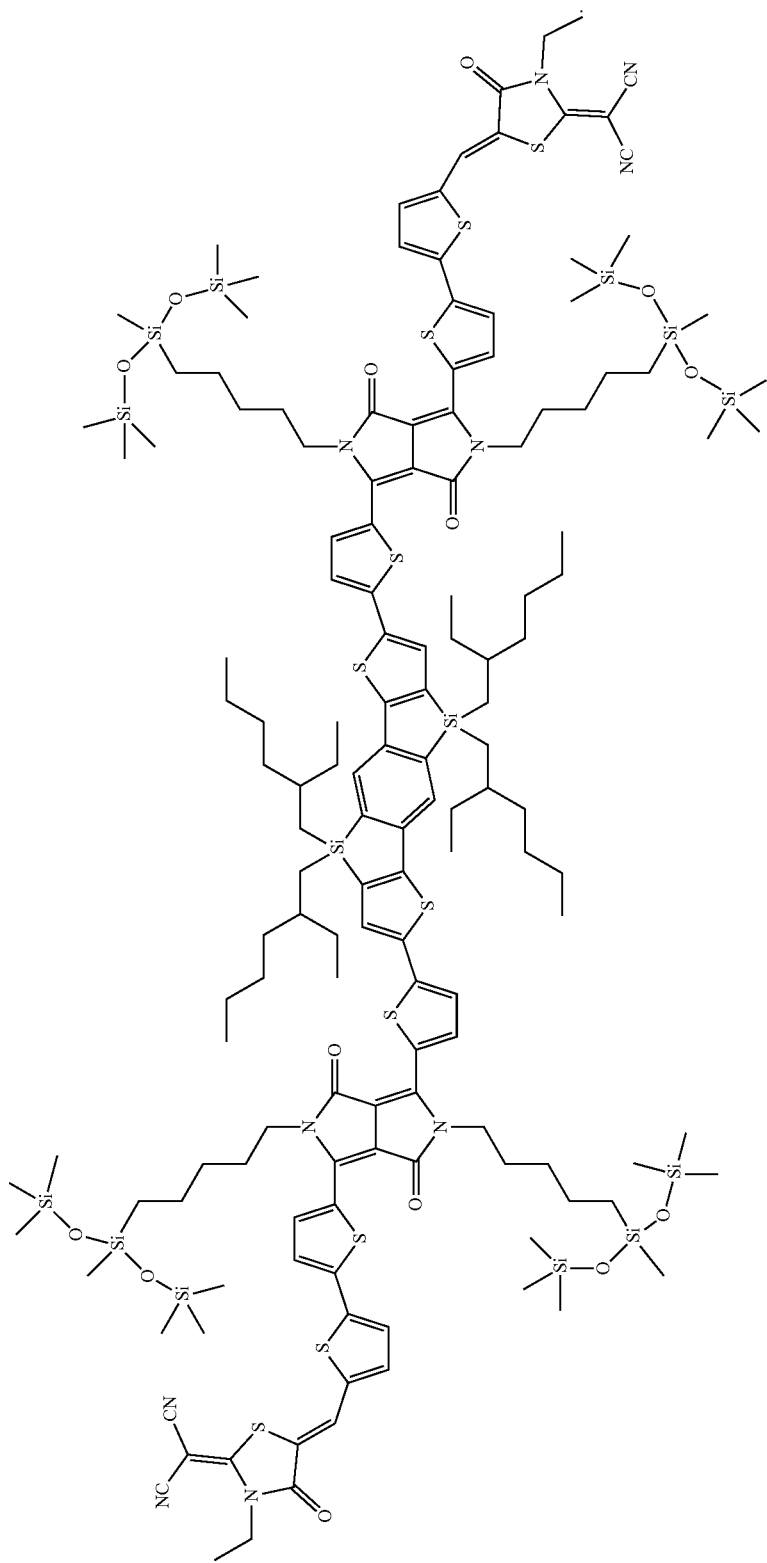

5. An organic solar cell comprising:
a first electrode;
a second electrode facing the first electrode; and
an organic material layer having one or more layers between the first electrode and the second electrode and comprising a photoactive layer,
wherein the one or more layers of the organic material layer comprise the heterocyclic compound according to claim 1.

6. The organic solar cell of claim 5, wherein the organic material layer comprises a hole transporting layer, a hole injection layer, or a layer which simultaneously transports and injects holes, and
the hole transporting layer, the hole injection layer, or the layer which simultaneously transports and injects holes comprises the heterocyclic compound.

7. The organic solar cell of claim 5, wherein the organic material layer comprises an electron injection layer, an electron transporting layer, or a layer which simultaneously injects and transports electrons, and
the electron injection layer, the electron transporting layer, or the layer which simultaneously injects and transports electrons comprises the heterocyclic compound.

8. The organic solar cell of claim 5, wherein the photoactive layer comprises one or two or more selected from the group consisting of an electron donor and an electron acceptor, and
the electron donor comprises the heterocyclic compound.

9. The organic solar cell of claim 8, wherein the electron donor and the electron acceptor constitute a bulk heterojunction (BHJ).

10. The organic solar cell of claim 5, wherein the photoactive layer has a bilayer thin film structure comprising an n-type organic material layer and a p-type organic material layer, and
the p-type organic material layer comprises the heterocyclic compound.

* * * * *